United States Patent
Shastri et al.

(10) Patent No.: US 6,471,993 B1
(45) Date of Patent: Oct. 29, 2002

(54) THREE-DIMENSIONAL POLYMER MATRICES

(75) Inventors: Venkatram R. Shastri, Allston; Ivan Martin, Somerville; Robert S. Langer, Newton; Joachim Seidel, Somerville, all of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/463,709

(22) PCT Filed: Jul. 31, 1998

(86) PCT No.: PCT/US98/16020

§ 371 (c)(1),
(2), (4) Date: Sep. 29, 2000

(87) PCT Pub. No.: WO99/09149

PCT Pub. Date: Feb. 25, 1999

Related U.S. Application Data

(63) Continuation of application No. 08/904,780, filed on Aug. 1, 1997, now abandoned.
(60) Provisional application No. 60/067,234, filed on Dec. 2, 1997, and provisional application No. 60/069,547, filed on Dec. 12, 1997.

(51) Int. Cl.[7] ................................................ A61K 9/14
(52) U.S. Cl. ........................ 424/486; 424/484; 424/487; 424/422; 424/423; 424/424; 424/425; 424/426; 514/772.3

(58) Field of Search .................................. 424/484, 486, 424/487, 422, 423, 424, 425, 426; 514/772.3

(56) References Cited

U.S. PATENT DOCUMENTS

| 4,100,238 A | 7/1978 | Shinomura | 264/49 |
| 4,186,448 A | 2/1980 | Brekke | 3/1.9 |

(List continued on next page.)

FOREIGN PATENT DOCUMENTS

EP  0 299 010 B1  6/1996

OTHER PUBLICATIONS

Lo et al., "Fabrication of controlled release biodegradable foams by phase separation," *Tissue Engineering* 1(1):15–28 (1995).
Mikos et al., "Preparation and characterization of poly(L-–lactic acid) foams," *Polymer* 35(5):1068–1077 (1994).
Mooney et al., "Novel approach to fabricate porous sponges of poly(D,L–lactic–co–glycolic acid) without the use of organic solvents," *Biomaterials* 17(14):1417–1422 (1996).

*Primary Examiner*—Thurman K. Page
*Assistant Examiner*—Liliana Di Nola-Baron
(74) *Attorney, Agent, or Firm*—Clark & Elbing LLP; Kristina Bieker-Brady

(57) ABSTRACT

Matrices that include a macrostructure having a semi-solid network and voids, and a microstructure having voids, in which the microstructure is located within the semi-solid network are disclosed. Methods for preparing these matrices are also disclosed.

29 Claims, 19 Drawing Sheets

U.S. PATENT DOCUMENTS

| | | | |
|---|---|---|---|
| 4,394,370 A | 7/1983 | Jefferies | 424/15 |
| 4,458,678 A | 7/1984 | Yannas et al. | 128/155 |
| 4,623,472 A | 11/1986 | Jamison et al. | 252/12.2 |
| 4,828,772 A | 5/1989 | Lopatin et al. | 264/45.9 |
| 4,963,489 A | 10/1990 | Naughton et al. | 435/240.1 |
| 5,041,138 A | 8/1991 | Vacanti et al. | 623/16 |
| 5,108,755 A | 4/1992 | Daniels et al. | 424/426 |
| 5,133,755 A | 7/1992 | Brekke | 623/16 |
| 5,139,529 A | 8/1992 | Seita et al. | 623/66 |
| 5,232,984 A | 8/1993 | Hubbell et al. | 525/54.1 |
| 5,328,695 A | 7/1994 | Lucas et al. | 424/426 |
| 5,352,574 A | 10/1994 | Guiseppi-Elie | 435/4 |
| 5,356,630 A | 10/1994 | Laurencin et al. | 424/426 |
| 5,366,508 A | 11/1994 | Brekke | 623/16 |
| 5,380,536 A | 1/1995 | Hubbell et al. | 424/497 |
| 5,393,848 A | 2/1995 | Charbonneau et al. | 525/425 |
| 5,514,378 A | 5/1996 | Mikos et al. | 424/425 |
| 5,518,680 A | 5/1996 | Cima et al. | 264/401 |
| 5,522,895 A | 6/1996 | Mikos | 623/16 |
| 5,529,914 A | 6/1996 | Hubbell et al. | 435/182 |
| 5,545,409 A | 8/1996 | Laurencin et al. | 424/426 |
| 5,567,435 A | 10/1996 | Hubbell et al. | 424/426 |
| 5,567,440 A | 10/1996 | Hubbell et al. | 424/484 |
| 5,573,934 A | 11/1996 | Hubbell et al. | 435/177 |
| 5,589,176 A | 12/1996 | Seare, Jr. | 424/400 |
| 5,605,693 A | 2/1997 | Seare, Jr. | 424/400 |
| 5,624,674 A | 4/1997 | Seare, Jr. | 424/400 |
| 5,626,861 A | 5/1997 | Laurencin et al. | 424/426 |
| 5,626,863 A | 5/1997 | Hubbell et al. | 424/426 |
| 5,627,233 A | 5/1997 | Hubbell et al. | 525/54.1 |
| 5,629,009 A | 5/1997 | Laurencin et al. | 424/426 |
| 5,654,381 A | 8/1997 | Hrkach et al. | 525/450 |
| 5,677,355 A | 10/1997 | Shalaby et al. | 521/61 |
| 5,681,572 A | 10/1997 | Seare, Jr. | 424/400 |
| 5,711,960 A * | 1/1998 | Shikinami | 424/426 |

* cited by examiner

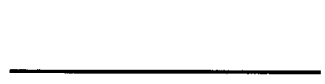
Fig. 6A   Fig. 6B
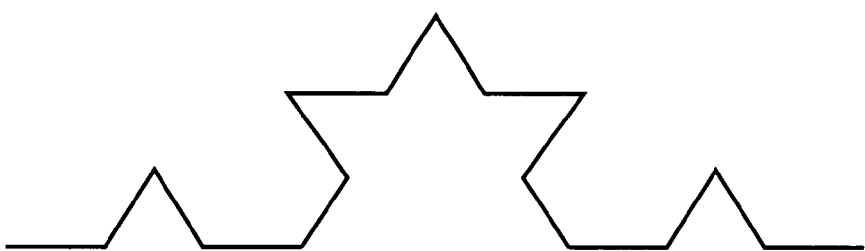
Fig. 6C
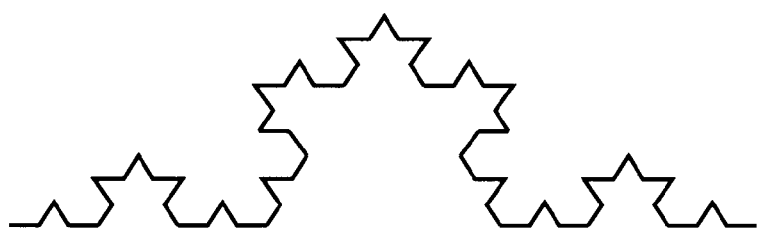
Fig. 6D

PHASE I: CELL EXPANSION    PHASE II: CELL SEEDING    PHASE III: CONSTRUCT CULTURE
IN MONOLAYER (2-3 WEEKS)   IN SPINNER FLASK (3 DAYS) IN MIXED PETRI DISH (25 DAYS)

INITIAL SCAFFOLD SIZE

THREE-DIMENSIONAL POLYMER MATRICES

This invention claims the benefits of provisional application No. 60/069,547, filed Dec. 12, 1997, and No. 60/067,234, filed Dec. 2, 1997, and a continuation of Ser. No. 08/904,780, filed on Aug. 1, 1997, now abandoned.

STATEMENT OF FEDERALLY SPONSORED RESEARCH

This invention was made with government support under Grant Number NIH-5R01-GM26698 awarded by the National Institutes of Health and Grant Number BES-9525913 m awarded by the National Science Foundation. The government has certain rights in the invention.

BACKGROUND OF THE INVENTION

The invention relates to porous polymer matrices.

Porous polymer media, such as membranes, macroporous solids, and cellular solids are used in a wide variety of applications. These materials are used as support structures for gas and solution phase catalysis; support structures for solid phase synthesis; immobilized beds in bioreactors; and thermal insulation.

Recent advances in the field of tissue engineering have led to new uses for these porous materials. Tissue engineering techniques provide alternatives to the prosthetic materials currently used in plastic and reconstructive surgery, and in joint repair and replacement; these techniques are also useful in the formation of organ equivalents to replace diseased, defective, or injured organs. Porous materials are used as scaffolds for the in vitro or in vivo growth and development of tissue. Because these materials are placed in the human body, they must often have structural and functional characteristics that differ from the requirements for materials used in non-therapeutic applications.

SUMMARY OF THE INVENTION

The invention features porous matrices that are useful in a variety of applications, including tissue engineering, electromagnetic shielding, and fuel cell applications.

In a first aspect, the invention features a matrix including a macrostructure having a semi-solid network and voids; the matrix further includes a microstructure, which preferably has voids; the microstructure is located within the semi-solid network. In a preferred matrix, the semi-solid network includes a polymer or a copolymer. The copolymer can have a carboxylic acid group or an amine group. Another preferred matrix includes a conductive polymer selected from the group consisting of polypyrrole, polyaniline, polyacetylene, and polythiophene.

In a preferred matrix, the semi-solid network consists essentially of a polymer or mixture of polymers. In another preferred matrix, the semi-solid network is substantially continuous.

The voids of the macrostructure can also be substantially continuous. The voids of the macrostructure and the voids of the microstructure can be connected or not connected. The voids of the macrostructure define openings. In a preferred matrix, the average diameter of the openings and the average diameter of the cross-sections of the semi-solid network have a ratio of from 2:1 to 10:1, and more preferably have a ratio of from 2:1 to 5:1.

In a preferred embodiment, a cubic matrix having dimensions of about 0.5 cm on all sides and having voids defining openings with an average diameter of 50–500 $\mu$m has a connectivity number of at least 10, and more preferably has a connectivity number of at least 20.

A ratio of the maximum diameter and the minimum diameter of a cross section of the semi-solid network of a preferred matrix is from 1:1 to 10:1, and more preferably is from 1:1 to 4:1, or from 1:1 to 2:1.

In another preferred matrix, at least 10% of the voids of the microstructure have a fractal dimension of at least 3; preferably, less than 10% of the voids of the macrostructure of this matrix have a fractal dimension higher than 1. A preferred matrix is three dimensional, and the exterior face of the matrix can be porous.

The matrix can include an additive, at least 5% of which is located within the microstructure; the preferred additive is selected from the group consisting of transition metal oxides, transition metal sulfates, transition metal carbonates, transition metal phosphates, transition metal nitrates, sodium carbonate, sodium phosphate, calcium carbonate, calcium phosphate, β-glycerophosphate, and hydroxyapatite having particle sizes of greater than 150 $\mu$m. The additive can also be selected from the group consisting of polyethylene fibers, polypropylene fibers, Teflon® (polytetrafluoroethylene) fibers, nylon fibers, and PGA fibers; it can also be selected from the group consisting of titanium fibers, titanium powder, and titanium dioxide; or from the group consisting of inorganic and organic reducing agents.

A preferred matrix has a porosity of at least about 20%, and more preferably has a porosity of at least about 40%, 70%, 90%, 92%, or 95%. A preferred matrix is biodegradable, bioerodible, or bioresorbable. The matrix can be permeable or impermeable to cells; it is preferably permeable to bodily fluids. A preferred matrix includes a living cell; preferably, the cell is selected from the group consisting of bone marrow cells, periosteal cells, chondrocytes, smooth muscle cells, endothelial cells, fibroblasts, epithelial cells, tenocytes, neuronal cells, Schwann cells, hepatocytes, Kupffer cells, fibroblasts, pancreatic islet cells, and cardiac myocytes. Another preferred matrix includes a bioactive agent, which is preferably contained in microspheres. The bioactive agent is selected from the group consisting of antibiotics, anesthetics, anti-inflammatory agents, contrast agents, and imaging agents.

A preferred matrix has a coating; less than 5% of the coating is contained in the voids of the microstructure. The coating may be attached to the matrix by electrostatic forces, by covalent bonding, or as a result of the shape of the coating. In this last case, the coating encases at least a portion of the matrix.

The matrix may be coated by any coating known to those skilled in the art to be appropriate, however, another preferred matrix is coated with a hydrophilic material selected from the group consisting of collagen, PEG, PEO, PVA, hydrogels, carboxylic acid-containing substances, fibronectin, vitronectin, laminin, and bone morphogenetic protein (BMP).

Yet another preferred matrix includes bioerodible fibers; the fibers preferably include PGA or therapeutic agents. Another preferred matrix includes a protein that is protected with a cyclodextrin.

A preferred matrix changes in size less than 50% when cells are added to the matrix; another preferred matrix has a compressive modulus which is higher than known polymer matrices having the same components in the same ratio. For example, a preferred matrix has a compressive modulus of at least 0.4 MPa at 4% strain. In addition, a preferred matrix is non-friable.

In a second aspect, the invention features a porous polymer matrix that changes in size less than 50% when cells are added to the matrix. A preferred matrix changes in size less than 25% when cells are added to the matrix, and more preferably changes in size less than 10%. In a preferred embodiment the change in matrix size is defined as that change which occurs over a limited time period, of over a period of less than ½ the time it takes for the matrix to degrade, preferably, less than 1/10 the time it takes for the matrix to degrade, most preferably, the period of time during which the initial cells are added to the matrix if such time is less than 1/10 the time it takes for the matrix to degrade.

A preferred matrix has a macrostructure having a semi-solid network and voids and a microstructure having voids; the microstructure is located within the semi-solid network. Preferably, the voids of the macrostructure are substantially continuous. A preferred matrix has a porosity of at least 90%, and more preferably has a porosity of at least 92%, or 95%. A preferred matrix is biodegradable, bioerodible or bioresorbable. A preferred matrix is permeable to bodily fluids. Another preferred matrix includes a living cell or a bioactive agent.

A preferred matrix has a coating; less than 5% of the coating is contained in the voids of the microstructure. The coating may be attached to the matrix by electrostatic forces, by covalent bonding, or as a result of the shape of the coating. In this last case, the coating encases at least a portion of the matrix.

The matrix may be coated with any suitable coating known to those skilled in the art, another preferred matrix is coated with a hydrophilic material selected from the group consisting of collagen, PEG, PEO, PVA, hydrogels, carboxylic acid-containing substances, fibronectin, vitronectin, laminin, and bone morphogenetic protein (BMP).

A preferred matrix is three dimensional. The exterior face of a preferred matrix is porous. Another preferred matrix includes an additive; at least 5% of the additive is located within the microstructure. A preferred matrix has a density of less than about 0.150 g/cc, and more preferably has a density of less than about 0.120 g/cc.

In a third aspect, the invention features a porous polymer matrix including poly(lactic acid) and/or poly(lactic acid-co-glycolic acid), and at least one hydrophilic polymer selected from the group consisting of poly(ethylene glycol), poly(ethylene oxide), polypropylene oxide, polypropylene glycol, poly(vinyl alcohol), a copolymer of polypropylene oxide and polyethylene oxide, collagen, gelatin, fibronectin, glycosaminoglycan, and polylysine. The poly(ethylene glycol) preferably has ester linkages. A preferred matrix includes a blend of poly(lactic acid), preferably poly(L-lactic acid), and poly(lactic acid-co-glycolic acid).

A preferred matrix includes at least 0.1% of the hydrophilic polymer, and more preferably includes at least 1% of the hydrophilic polymer, at least 5% of the hydrophilic polymer, at least 10% of the hydrophilic polymer, or at least 20% of the hydrophilic polymer.

Preferably, the matrix includes at least one additive selected from the group consisting of calcium carbonate, β-glycerophosphate, calcium phosphate, sodium phosphate, sodium carbonate, sodium bicarbonate, and sodium chloride.

A preferred matrix includes calcium carbonate having particle sizes ranging from 5 μm to 500 μm. Preferably, the matrix includes 50–100% by weight of calcium carbonate, relative to the weight of poly(lactic acid) or poly(lactic acid-co-glycolic acid), or to the combined weight of poly (lactic acid) and poly(lactic acid-co-glycolic acid), if the matrix includes both of these polymers.

Another preferred matrix includes β-glycerophosphate having particle sizes ranging from 5 μm to 500 μm. Preferably the matrix includes 50–100% by weight of β-glycerophosphate, relative to the weight of poly(lactic acid) or poly(lactic acid-co-glycolic acid), or to the combined weight of poly(lactic acid) and poly(lactic acid-co-glycolic acid), if the matrix includes both of these polymers.

Another preferred matrix includes hydroxyapatite having particle sizes of at least 150 μm. The matrix preferably includes between 5 and 150% by weight of hydroxyapatite, relative to the weight of the polymer.

A preferred matrix has a macrostructure having a semi-solid network and voids; the matrix further includes a microstructure having voids; the microstructure is located within the semi-solid network. A preferred matrix has a porosity of at least about 90%. Another preferred matrix includes a living cell or a bioactive agent. A preferred matrix is three dimensional. Preferably, the exterior face of the matrix is porous.

A preferred matrix includes an additive; at least 5% of the additive is located within the microstructure. Preferably, the matrix changes in size less than 50% when cells are added to the matrix. A preferred matrix has a density of less than about 0.150 g/cc, and more preferably has a density of less than about 0.120 g/cc.

In a fourth aspect, the invention features a porous matrix consisting essentially of a polymer, or a mixture of polymers, where the matrix has a compressive modulus which is higher than known polymer matrices having the same components in the same ratio. For example, a preferred matrix has a compressive modulus of at least 0.4 MPa at 4% strain. Preferably, the matrix has a porosity of at least about 90%. A preferred matrix is biodegradable, bioerodible, or bioresorbable. Preferably, the matrix includes a living cell or a bioactive agent.

A preferred matrix has a coating; less than 5% of the coating is contained in the voids of the microstructure. The coating may be attached to the matrix by electrostatic forces, by covalent bonding, or as a result of the shape of the coating. In this last case, the coating encases at least a portion of the matrix.

While the matrix may be coated with any suitable coating known to those skilled in the art, another preferred matrix is coated with a hydrophilic material selected from the group consisting of collagen, PEG, PEO, PVA, hydrogels, carboxylic acid-containing substances, fibronectin, vitronectin, laminin, and bone morphogenetic protein (BMP).

A preferred matrix is substantially free of hydroxyapatite. A preferred matrix is three dimensional. Preferably, the exterior face of the matrix is porous. A preferred matrix includes an additive; at least 5% of the additive is located within the microstructure. A preferred matrix changes in size less than 50% when cells are added to the matrix. A preferred matrix has a density of less than about 0.150 g/cc, and more preferably has a density of less than about 0.120 g/cc.

In a fifth aspect, the invention features a matrix having a porosity of at least 90%. A preferred matrix is biodegradable, bioerodible, or bioresorbable. Preferably, the matrix includes a living cell or a bioactive agent.

A preferred matrix has a coating; less than 5% of the coating is contained in the voids of the microstructure. The coating may be attached to the matrix by electrostatic forces, by covalent bonding, or as a result of the shape of the coating. In this last case, the coating encases at least a portion of the matrix.

Another preferred matrix is coated with a hydrophilic material selected from the group consisting of collagen, PEG, PEO, PVA, hydrogels, carboxylic acid-containing substances, fibronectin, vitronectin, laminin, and bone morphogenetic protein (BMP). Preferably, the matrix is substantially free of hydroxyapatite. A preferred matrix is three dimensional. Preferably, the matrix changes in size less than 50% when cells are added to the matrix.

In a sixth aspect, the invention features a porous polymer matrix that bioerodes at substantially the same rate that cells populate the matrix. A preferred matrix has a porosity of at least about 90%. Preferably, the matrix includes a bioactive agent.

A preferred matrix has a coating; less than 5% of the coating is contained in the voids of the microstructure. The coating may be attached to the matrix by electrostatic forces, by covalent bonding, or as a result of the shape of the coating. In this last case, the coating encases at least a portion of the matrix.

Another preferred matrix is coated with a hydrophilic material selected from the group consisting of collagen, PEG, PEO, PVA, hydrogels, carboxylic acid-containing substances, fibronectin, vitronectin, laminin, and bone morphogenetic protein (BMP).

A preferred matrix changes in size less than 50% when cells are added to the matrix. Preferably, the matrix has a compressive modulus which is higher than known polymer matrices having the same components in the same ratio. For example, a preferred matrix has a compressive modulus of at least 0.4 MPa at 4% strain.

In a seventh aspect, the invention features a porous polymer matrix that bioerodes at substantially the same rate that tissue ingrows into the matrix.

In an eighth aspect, the invention features a porous polymer matrix that bioerodes at substantially the same rate that tissue remodeling occurs within the matrix.

In a ninth aspect, the invention features a composition including two layers, each layer including a matrix having voids, where the first layer has voids with an average size of less than 50 $\mu$m, and the second layer has voids with an average size of greater than 100 $\mu$m.

In a tenth aspect, the invention features a porous polymeric fiber. Preferably, the fiber includes a macrostructure having a semi-solid network and voids and a microstructure having voids, where the microstructure is located within the semi-solid network. In a preferred fiber, the voids are elongated and oriented in the same direction. Preferably, the fiber includes a bioactive agent.

In an eleventh aspect, the invention features a polymer matrix including an additive selected from the group consisting of transition metal oxides, transition metal sulfates, transition metal carbonates, transition metal phosphates, transition metal nitrates, sodium carbonate, sodium phosphate, calcium carbonate, calcium phosphate, β-glycerophosphate, and hydroxyapatite having particle sizes of greater than 150 $\mu$m.

In a twelfth aspect, the invention features a method of making a porous polymer matrix using a composition including a solvent, a porogen, and a polymer, where at least 50%, and more preferably at least 80%, or at least 90% of the solvent and the porogen are recovered. Preferably, the porogen is biodegradable.

In a thirteenth aspect, the invention features a method of making a porous polymer matrix. The method includes (a) combining a polymer solution and a porogen to form a mixture, and (b) extracting the porogen from the mixture and precipitating the polymer substantially simultaneously. The step of combining the polymer solution and the porogen can include depositing the polymer solution around the porogen using a three-dimensional printing technique. Preferably, the matrix is bounded on all sides during step (b). Preferably, the porogen is cryo-milled prior to step (a). The solvent is preferably removed by lyophilization. In a preferred method, a protein stabilized with a cyclodextrin is combined with the polymer and the porogen in step (a).

In a fourteenth aspect, the invention features a method of making a porous polymer matrix. The method includes (a) combining a polymer solution and an irregularly shaped porogen to form a mixture; and (b) extracting the porogen from the mixture.

In a fifteenth aspect, the invention features a method of making a porous polymer matrix; the method includes (a) combining a polymer solution and a porogen that has been cryo-milled to form a mixture; and (b) extracting the porogen from the mixture.

In a sixteenth aspect, the invention features a composition consisting essentially of irregularly shaped and sized wax particles. Preferably, at least 90% of the wax particles are smaller than 5000 $\mu$m.

In a seventeenth aspect, the invention features a method of making wax particles that includes cryo-milling wax. The invention further features a composition consisting essentially of a plurality of wax particles that are formed by cryo-milling wax. The invention also features a porous matrix including voids, where at least 10% of the voids in the matrix are made using this composition.

In an eighteenth aspect, the invention features a method of making wax particles; the method includes spraying the wax in a liquid solution or a liquid form into a coolant. The invention also features a composition consisting essentially of a plurality of wax particles formed by this method. The invention further features a porous matrix including voids, where at least 10% of the voids in the matrix are made using this composition.

In a nineteenth aspect, the invention features a method for controlling the mechanical strength of a porous polymer matrix that includes a water insoluble polymer and a water soluble polymer; the mechanical strength of the matrix may be optimized by alterations in the ratio of the water insoluble polymer and the water soluble polymer. Preferably, the porosity of the matrix remains substantially unchanged.

In a twentieth aspect, the invention features a method for controlling the degradation rate of a porous polymer matrix that includes a water insoluble polymer and a water soluble polymer; the method includes altering the ratio of the water insoluble polymer and the water soluble polymer. Preferably, the porosity of the matrix remains substantially unchanged.

In a twenty-first aspect, the invention features a mold for shaping an object; the mold has a plurality of sides, each of which defines a plurality of openings; at least two of the sides are permanently joined, and at least one side is detachable. Preferably, the mold includes Teflon® (polytetrafluoroethylene).

In a twenty-second aspect, the invention features a method for preparing a three dimensional porous polymer matrix including the steps of: (a) preparing a polymer solution; (b) adding particles with a size of less than 5000 $\mu$m to the polymer solution that are insoluble or sparingly soluble in the polymer solvent at the temperature of the polymer solution when the particles are added; (c) mixing the solid particles and the solution to form a polymer/particle mixture; and (d) extracting the particles from the polymer/particle mixture with a solvent that is a solvent for the particles and a non-solvent for the polymer. In preferred embodiments: the polymer/particle mixture has a consistency between that of a viscous liquid and that of a paste; the method further includes molding or extruding the polymer/particle mixture before the particles are extracted; the method further includes removing the remaining solvent by evaporation; or the polymer is a water-soluble polymer, such as collagen, polyethylene glycol, polyethylene oxide, polyvinyl alcohol, polyethylene oxide-polypropylene oxide copolymer, polyvinyl pyrrolidone, protein, peptide, or cellulose.

In another preferred embodiment, the polymer is a water-insoluble polymer, and can be selected from the group consisting of polyesters, poly(ester amides), polyamides, polyanhydrides, polyorthoesters, polycarbonates, polyurethanes, polyethers and poly(ether esters). In another preferred embodiment, the particles are made from a material selected from the group consisting of natural waxes, synthetic waxes and wax-like polymers; the particles can also be selected from the group consisting of paraffin, beeswax, and low density polyethylene. The size of the particles is preferably between about 50 and 500 $\mu$m.

In preferred embodiments, the polymer/particle mixture includes a component selected from the group consisting of industrial catalysts, diagnostic agents and therapeutic agents. The therapeutic agents can be selected from the group consisting of cells, osteoinductive materials and osteoconductive materials.

In a twenty-third aspect, the invention features a porous polymer matrix prepared by: (a) preparing a polymer solution; (b) adding to the solution an effective amount of solid particles with a size of less than 5000 $\mu$m that are insoluble or sparingly soluble in the polymer solvent at the temperature of the polymer solution when the particles are added; (c) mixing the solid particles and the solution to form a polymer/particle mixture; and (d) extracting the particles from the polymer/particle mixture with a solvent that is a solvent for the particles and a non-solvent for the polymer while simultaneously precipitating the polymer. Preferably, the polymer/particle mixture has a consistency between that of a viscous liquid and that of a paste. A preferred matrix is made by molding or extruding the polymer/particle mixture before the particles are extracted.

The polymer can be a water-soluble polymer, and can be selected from the group consisting of collagens, polyethylene glycols, polyethylene oxides, polyvinyl alcohols, polyethylene oxide-polypropylene oxide copolymers, polyvinyl pyrrolidones, proteins, peptides, and celluloses. In other embodiments, the polymer is a water-insoluble polymer, and can be selected from the group consisting of polyesters, poly(ester amides), polyamides, polyanhydrides, polyorthoesters, polycarbonates, polyurethanes, polyethers and poly(ether esters).

The particles can be particles of natural waxes, synthetic waxes and wax-like polymers. The waxes and wax-like polymers can be selected from the group consisting of paraffin, beeswax, and low density polyethylene. In other embodiments, the particles are polymer particles. Preferably the size of the particles is between about 50 and 500 $\mu$m.

In other preferred embodiments, the polymer/particle mixture includes a component selected from the group consisting of industrial catalysts, diagnostic agents, therapeutic agents. The therapeutic agent can be selected from the group consisting of cells, osteoinductive materials, and osteoconductive materials.

The matrix can be formed into the shape of a hollow tube; formed into a solid object selected from the group consisting of rods, pins, screws, plates and anatomical shapes; formed into a solid object selected from the group consisting of porous electrodes, porous fibers, and porous solid support materials; or formed into particles suitable for pulmonary delivery or injection.

In a twenty-fourth aspect, the invention features a polymer matrix with a porosity between about 10 and 95% which is substantially uniform throughout the matrix, prepared by (a) dissolving a water-soluble polymer in a solution; (b) adding particles with a size of less than 5000 $\mu$m to the polymer solution that are insoluble or sparingly soluble in the polymer solvent at the temperature of the polymer solution when the particles are added; (c) mixing the solid particles and the solution to form a polymer/particle mixture; and (d) extracting the particles from the polymer/particle mixture with a solvent that is a solvent for the particles and a non-solvent for the polymer.

"Porous polymer matrix" means any solid object made of a polymer, which forms a continuous or discontinuous porous network. Porous polymer matrices include porous membranes, porous foams, and porous beads.

"Macrostructure," as used herein when referring to a matrix, means the semi-solid network of the matrix and the continuous voids defined by the network.

"Microstructure," as used herein when referring to a matrix, means the system of voids that are contained within the semi-solid network of the matrix.

"Semi-solid," as used herein when referring to a structure, means that the structure can have voids.

"Voids" mean portions of a matrix that do not contain the material that makes up the semi-solid network of the matrix; the voids are filled with any substance that is different from the substance that makes up the majority of the semi-solid network.

The "diameter of a void" means the diameter of the largest sphere that would fit through the opening defined by the void.

"Connectivity number" means the number of cuts that must be made in order to ensure that an object is separated into at least two completely separate pieces.

A "cut" means a cut that passes through a meridional circle of the semi-solid network and does not pass through a void of the matrix.

A "cross-section" means a section that can be drawn through a portion of the semi-solid network of the matrix by drawing a meridional curve on the exterior surface of the portion.

A "minimum diameter of a cross section" means the shortest straight line that can be drawn that joins two edges of the cross-section and passes through the center of the cross-section.

A "maximum diameter of a cross section" means the longest straight line that can be drawn that joins two edges of the cross-section.

A "diameter of a cross-section" is the mean of the minimum and maximum diameters.

"Average diameter of the cross sections of the semi-solid network," means the mean of the diameters of the cross sections of the semi-solid network.

"Continuous," as used herein when referring to the semi-solid network, means that the relevant portions of the semi-solid network are joined as one piece. That is, a line can be drawn from one point on the surface to another point without leaving the surface of the semi-solid network and without crossing a void. Similarly, continuous, as used herein when referring to voids, means that a line can be drawn connecting a point in the void space with another point in the void space, without leaving the void space and without crossing the semi-solid network.

"Fractal," as used herein, means an irregular curve or shape that repeats itself over a continuous surface at different scales.

An "exterior face of the matrix" means the face that is adjacent to the mold during formation of the matrix.

"Porogen," as used herein, means a non-gaseous material that is soluble in at least one solvent and sparingly soluble in at least one solvent, that is combined with a material to form a mixture, then removed from the mixture to leave voids.

"Sparingly soluble" describes a material that, under the conditions of processing, has a solubility of less than 30% by weight in the given solvent, and preferably has a solubility of less than 20% by weight, less than 10% by weight, or less than 2% by weight.

"Non-solvent," as used herein, describes a solvent in which a given material is insoluble or sparingly soluble.

"Hydrophilic" describes a material that has a solubility of at least 0.5% by weight in water.

"Microspheres" describe objects having an average diameter of about 2 μm to about 100 μm. They are composed of synthetic polymers, biological polymers, or blends or combinations thereof.

"Bioactive agent" describes a substance that has a physiological or biological effect on a cell, tissue, organ, or other living structure.

"Biodegradable" means capable of being broken down into innocuous products when placed within a living system, such as a cell culture system, or a living organism, such as a human or animal, or when exposed to bodily fluids.

"Bioerodible" means capable of being dissolved or suspended in biological fluids.

"Bioresorbable" means capable of being absorbed by the cells, tissue, or fluid in a living body.

"Bioerodes at substantially the same rate that cells populate" means that an object, such as a matrix, bioerodes—that is, is dissolved or suspended in biological fluids—at the same rate that cells grow and produce extracellular matrix (ECM), so that the total volume of the matrix material, the cells, and the ECM within the matrix remains substantially constant.

"Substantially constant," when referring to the total volume of the matrix material, the cells, and the extracellular matrix within the matrix, means a change in the total volume of less than 25%, and preferably less than 15%, or 5%.

"Impermeable," as used herein, means that cells can migrate into the material to a depth of less than 200 μm. "Three-dimensional," as used herein, means that the smallest dimension of an object (e.g., length, width, or depth) is at least 100 μm.

"Non-friable" means that when cut, the portions separate into masses with a total loss of materials to flaking or powdering being less than 5% of the total mass of the material.

The matrices of the invention offer several advantages over existing matrices. The porous nature of the matrices and the high surface areas provide an environment that is permissive to cell ingrowth. In addition, the highly interconnected structure of the matrices provides them with mechanical strength.

The methods of the invention provide convenient, cost-effective ways to prepare porous polymer matrices. In addition, the methods of the invention provide novel ways to alter physical properties of the matrices.

BRIEF DESCRIPTION OF THE DRAWINGS

FIG. 6A is a schematic representation of a curve with a fractal dimension of zero; FIG. 6B is a schematic representation of a curve with a fractal dimension of 1; FIG. 6C is a schematic representation of a curve with a fractal dimension of 2; and FIG. 6D is a schematic representation of a curve with a fractal dimension of 3.

FIG. 11A is a photograph of a cross section of a bovine bone marrow stromal cell and PLA matrix construct; FIG. 11B is a photograph of a cross section of a bovine bone marrow stromal cell and PLA matrix construct grown in the presence of β-glycerophosphate and dexamethasone; and FIG. 11C is a photograph of a cross section of a bovine bone marrow stromal cell and PLA/PEG/calcium carbonate matrix construct grown in the presence of β-glycerophosphate and dexamethasone.

FIG. 14A is a photograph of a cross section of a bovine chondrocyte and PLA matrix construct; FIG. 14B is a photograph of a cross section of a bovine chondrocyte and PLA/PEG (80:20) matrix construct; and FIG. 14C is a photograph of a cross section of a bovine chondrocyte and PLA/PEG (60:40) matrix construct.

DESCRIPTION OF THE PREFERRED EMBODIMENTS

Figure 1A:
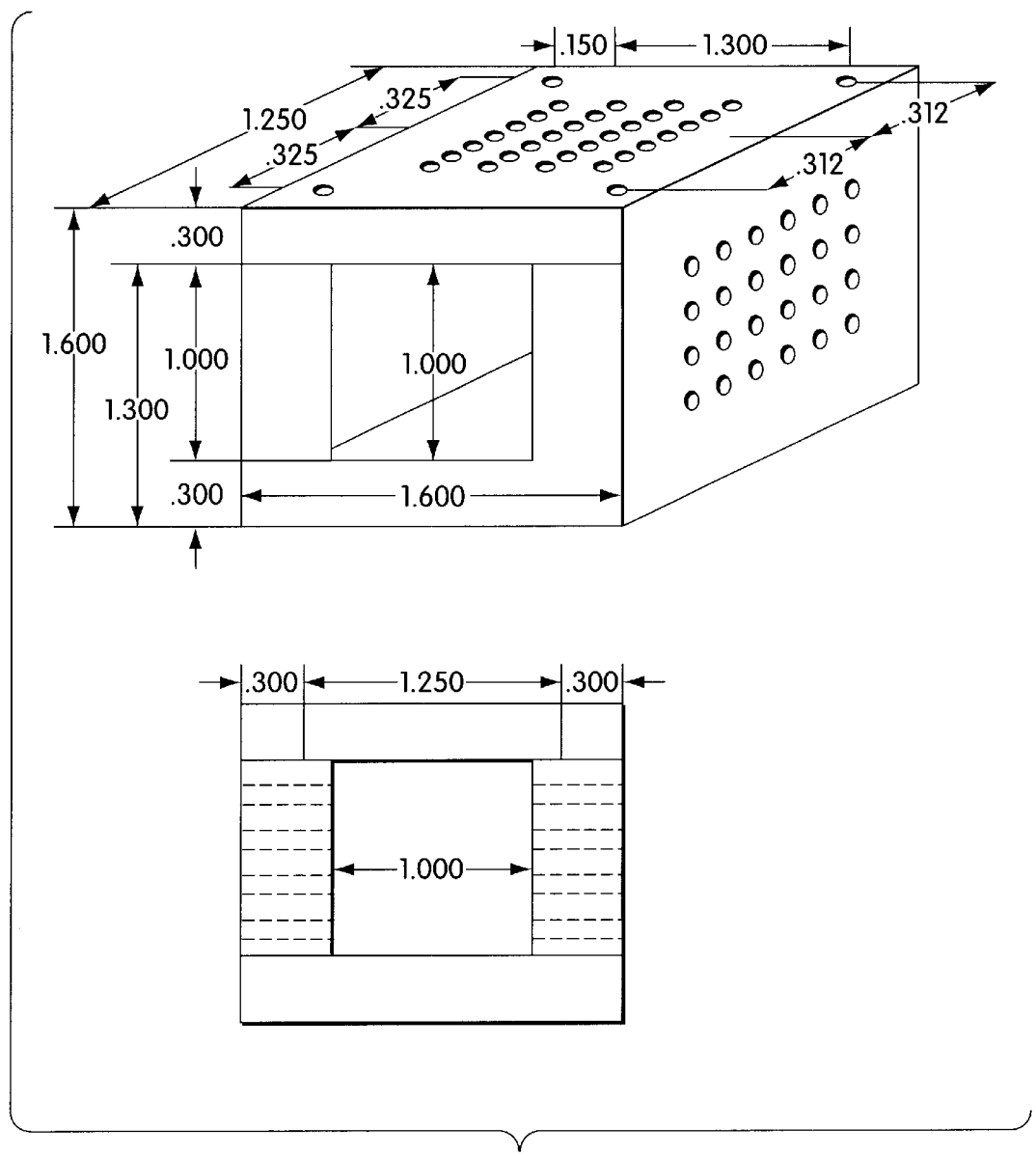
FIG. 1A is a schematic representation of a mold used to make matrices of the invention.

The matrices of the invention have a porous macrostructure and preferably have a porous microstructure. They are easy to prepare and have a number of unique properties.

Methods for Preparing Matrices

The matrices are prepared by dissolving a polymer in a suitable solvent (referred to as a polymer solvent), then adding solid particles of a material that is insoluble or sparingly soluble in the polymer solvent (the solid particles are referred to herein as porogens) at a temperature at which the particles are blended with the polymer solution, and combining to form a slurry having a consistency ranging between that of a viscous liquid and that of a paste. The viscosity of the polymer/particle blend will vary depending on the types of polymer used, the solvent, and the temperature. Preferably, the polymer solution includes between 50 and 250 grams of polymer per liter of solution.

The slurry is then shaped by being molded or extruded. The shaped slurry is treated with a solvent in which the porogen is soluble, and in which the polymer is insoluble or sparingly soluble (referred to as the porogen solvent). The polymer precipitates in this solvent; at the same time, the porogen is extracted from the mixture. Preferably, the amount of solvent used to extract the particles is more than the minimal amount of solvent required to dissolve the particles at the temperature at which the particles are extracted.

The precipitated polymer forms a continuous, preferably interconnected or reticulated, porous network. The simultaneous precipitation/extraction gives the polymer matrix unique properties. After the initial extraction of the solid particles, the matrix can be subjected to additional extractions to remove residual porogen. The extractions can be done, for example, in a beaker, or in a Soxhlet extraction apparatus. The additional extraction steps, and the continuous nature of the voids, help to ensure that essentially all of the porogen is removed from the finished matrix.

Alternatively, the polymer/polymer solvent/porogen slurry can be formed by dissolving a polymer in a solvent, then depositing this solution around porogen particles using a free form fabrication technique, such as three-dimensional printing. For example, the slurry can be shaped using the three-dimensional printing techniques described in Cima et al., U.S. Pat. No. 5,518,680, entitled "Tissue Regeneration Matrices by Solid Free Form Fabrication Techniques."

The method is extremely versatile. The precipitation/ extraction step can take place at any temperature at which the polymer does not melt, degrade, or, in the case of proteins, denature. Low temperature extractions, for example, using supercritical fluids such as liquid carbon dioxide, may be preferred for certain applications.

The method can be used to generate matrices of a wide variety of shapes and sizes, including three-dimensional matrices. In addition, the method can be scaled up simply by increasing the amounts of polymer, polymer solvent, porogen, and porogen solvent used, and by using a larger mold. The method is advantageous because polymer matrices can be prepared in a relatively short period of time.

Any polymer that is soluble in at least one solvent can be used to make the matrices of the invention. The polymers can be water soluble or insoluble; biodegradable or non-biodegradable; natural or synthetic. Biodegradable polymers are preferred for tissue engineering applications. Synthetic polymers are preferred for this application as well, since they degrade in a more reproducible manner than natural polymers.

Synthetic polymers which can be used in the present invention include poly(hydroxy acids) such as poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), polyanhydrides, polyorthoesters, poly(ester amides), polyamides, poly(ester ethers)polycarbonates, polyalkylenes such as polyethylene and polypropylene, polyalkylene glycols such as poly (ethylene glycol) (PEG), polyalkylene oxides such as poly (ethylene oxide) (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, poly(propylene fumarate), polyoxymethylene, and poloxamers.

The polymers can optionally include one or more photopolymerizable groups. The polymers can also be derivatizated. For example, the polymers can have substitutions such as alkyl groups, alkylene groups, or other chemical groups. The polymers can also be hydroxylated oxidized, or modified in some other way familiar to those skilled in the art. Blends and co-polymers of these polymers can also be used.

Preferred non-biodegradable polymers include ethylene vinyl acetate, polyacrylic acids, polyamides, and copolymers and blends thereof.

Preferred biodegradable polymers include poly(hydroxy acids) such as PLA, PGA, PLGA, and copolymers with PEG; polyanhydrides, poly(ortho)esters, polyurethanes, poly(butyric acid), poly(valeric acid), poly(lactide-co-caprolactone), trimethylene carbonate, and the polymers described in Hubbell et al., U.S. Pat. Nos. 5,654,381; 5,627,233; 5,628,863; 5,567,440; and 5,567,435. In general, these materials degrade in vivo by both non-enzymatic and enzymatic hydrolysis, and by surface or bulk erosion.

Preferred water-soluble polymers include polyethylene oxides, polyethylene glycols, ethylene oxide-propylene oxide copolymers (poloxamers and poloxamines), polyvinyl alcohols, polyvinylpyrrolidones, poly(acrylic acids), and copolymers and blends thereof.

Natural polymers that can be used in the invention include polysaccharides such as alginate, dextran, and celluloses; collagens, including derivatized collagens (e.g., alkylated, hydroxylated, oxidized, or PEG-lated collagens, as well as collagens modified by other alterations routinely made by those skilled in the art); hydrophilic proteins such as albumin; hydrophobic proteins such as protamines, and copolymers and mixtures thereof. In general, these materials degrade by enzymatic hydrolysis, by exposure to water in vivo, or by surface or bulk erosion.

Preferred bioadhesive polymers include polyanhydrides and polyacrylic acids. In one embodiment, reactive groups on the polymers, for example, hydroxy, amine, carboxylic acid, thiol, anhydride, ester and vinyl groups, are reacted with reactive groups on agents to be incorporated into the polymer matrix. For example, bioactive compounds such as proteins contain reactive amine groups which can be coupled with reactive carboxylic acid, ester, or anhydride groups on the polymer to form polymers that are covalently bonded to the compounds. In another embodiment, ion pairs are formed between acidic or basic groups on a polymer and basic or acidic groups on a bioactive compound to form a polymer that is ionically bonded to the compounds. Those of skill in the art can readily determine an appropriate bioactive compound and polymer to couple by forming ionic or covalent bonds, and can also readily determine appropriate reaction conditions for forming such bonds.

One factor to be considered when selecting an appropriate polymer is the time required for in vivo stability, i.e., the time in which the polymer matrix is required to degrade, in those embodiments in which the matrix is used in vivo. Preferably, the polymer matrix exhibits an in vivo stability between approximately a few minutes and one year. When used for drug delivery, the in vivo stability is preferably between a few hours and two months. When used for tissue engineering, the in vivo stability is preferably between one week and several months.

Preferred polymers have a molecular weight of at least 40,000 daltons.

Materials that can be used as porogens include waxes, such as paraffin, bees wax, and carnuba wax, and wax-like substances, such as low melting or high melting low density polyethylene (LDPE), and petroleum jelly. Other materials include hydrogels such as PEG, alginate, bone wax (fatty acid dimers), fatty acid esters such as mono-, di-, and tri-glycerides, cholesterol and cholesterol esters, and naphthalene. In addition, synthetic or biological polymeric materials such as proteins can be used.

The particles are in a solid state, rather than a liquid or fluent state; the particles may be porous solid particles. The particles must be insoluble or sparingly soluble in the polymer solvent at the temperature at which the polymer and the particles are blended. The particles must also be soluble in a solvent in which the polymer is insoluble or sparingly soluble, and in which the polymer precipitates at the temperature at which the particles are extracted.

The size of the porogen particles used in the invention is preferably less than 5000 µm, and is more preferably between 500 and 5000 µm, or 25 and 500 µm. Particles of the desired size can be prepared, for example, by cryo-milling the particles. Cryo-milling involves cooling the solid material to a suitable temperature, i.e., one at which the particles will not melt during the milling process, and milling the particles. The material can be cooled, for example using coolants such as liquid nitrogen, liquid carbon dioxide, and dry ice. For example, wax can be cooled in liquid nitrogen, and then milled to the desired particle size.

Alternatively, liquid material (i.e., dissolved or melted) can be sprayed into a non-solvent for the material, and the particle size can be controlled by controlling the size of the droplets. Suitable solvents include acetone, ethyl acetate, dimethylsulfoxide (DMSO), dimethylformamide (DMF), water, ethers, glymes, glycerol, ethylene glycol, xylene, chloroform, methylene chloride, toluene, and alcohols. In one embodiment, liquid material is sprayed into a coolant, such as liquid nitrogen.

The polymer solvents are solvents in which the polymer dissolves, and in which the solid particles are insoluble or sparingly soluble. The solvent used will depend on the type of polymer and the type of solid particles. For example, some polymers are soluble in halogenated solvents, such as methylene chloride, chloroform, carbon tetrachloride, dichloroethane, trichloroethylene, and hexafluoroisopropanol. Water-soluble polymers can be dissolved or dispersed in water or relatively polar organic solvents such as alcohols, ethyl acetate, acetone, dimethylsulfoxide, dimethylformamide, ethers, glymes, phenols, and chloroform. Those of skill in the art can readily determine an appropriate solvent for dissolving a polymer, in which the solid particles are insoluble or sparingly soluble. The solvent is preferably volatile, so that remaining solvent can be removed while the matrix is formed, or after the matrix is formed. Preferred polymer solvents include xylene, acetone, and halogenated solvents such as dichloromethane (methylene chloride), chloroform, carbon tetrachloride, dichloroethane, trichloroethane, and hexafluoroisopropanol.

Examples of suitable porogen solvents include hydrocarbon solvents such as pentanes, hexanes, heptanes, octanes, benzene, toluene, xylenes, cresols, and vegetable oils. Another suitable solvent is petroleum ether. Volatile solvents are preferred in most embodiments, because residual amounts of these solvents can be readily removed from the resulting polymer matrix once the wax has been extracted.

The following table summarizes examples of a number of polymers, polymer solvents, porogens, and porogen solvents that can be used in combination.

This table is meant to illustrate combinations that can be used in the present invention, and is not intended to be limiting.

TABLE 1

Combinations of Polymer, Polymer Solvent, Porogen, and Porogen Solvent

| Polymer | Polymer Solvent | Porogen | Porogen Solvent |
| --- | --- | --- | --- |
| polylactide, polyglycolide | acetone, ethyl acetate, methylene chloride, chloroform, hexafluoro-isopropanol, chlorinated aromatic hydrocarbons | paraffin, wax, bees wax, carnuba wax, petroleum jelly, monoglycerides, diglycerides, triglycerides, cholesterol, cholesterol esters | hexane, pentane, other aliphatic hydrocarbons, petroleum ether |
| polyglycolic acid (PGA) (amorphous) | hexafluoro-isopropanol | PLA, PGA, PCL, PS, PMMA | hexane, pentane, other aliphatic hydrocarbons, petroleum ether |
| polyglycolic acid (PGA) (amorphous) | hexafluoro-isopropanol | paraffin, wax, bees wax, carnuba wax, petroleum jelly, monoglycerides, diglycerides, triglycerides, | hexane, pentane, other aliphatic hydrocarbons, petroleum ether |

TABLE 1-continued

Combinations of Polymer, Polymer Solvent, Porogen, and Porogen Solvent

| Polymer | Polymer Solvent | Porogen | Porogen Solvent |
|---|---|---|---|
| poly(ε-capro-lactone) (PCL) | chlorinated hydrocarbons or tetrahydrofuran (THF) | cholesterol, cholesterol esters paraffin, wax, bees wax, carnuba wax, petroleum jelly, monoglycerides, diglycerides, triglycerides, cholesterol, cholesterol esters | hexane, pentane, other aliphatic hydrocarbons, petroleum ether |
| poly(methyl methacrylate) (PMMA), polycarbonate, polystyrene | acetone, tetrahydrofuran, chlorinated and fluorinated aliphatic hydrocarbons | paraffin, wax, bees wax, carnuba wax, petroleum jelly, monoglycerides, diglycerides, triglyccrides, cholesterol, cholesterol esters | hexane, pentane, other aliphatic hydrocarbons, petroleum ether |
| poly(vinyl-chloride), poly (vinylidine-difluoride | acetone, ethyl methyl ketone, diethyl ketone | paraffin, wax, bees wax, carnuba wax, petroleum jelly, monoglycerides, diglycerides, triglycerides, cholesterol, cholesterol esters | hexane, pentane, other aliphatic hydrocarbons, petroleum ether |
| polyvinyl alcohol | water, ethanol | paraffin, wax, bees wax, carnuba wax, petroleum jelly, monoglycerides, diglycerides, triglycerides, cholesterol, cholesterol esters | aliphatic hydrocarbons, aromatic hydrocarbons, acetone, mixtures thereof, petroleum ether |
| polyethylene glycol, polyethylene oxide | water, methylene chloride, chloroform, ethanol, propanol, hexafluoroisopropanol | paraffin, wax, bees wax, carnuba wax, petroleum jelly, monoglycerides, diglycerides, triglycerides, cholesterol, cholesterol esters | aliphatic hydrocarbons, aromatic hydrocarbons, acetone, mixtures thereof, petroleum ether |
| linear polyurethane | tetrahydrofuran, methylene chloride, chloroform, hexafluoroisopropanol | paraffin, wax, bees wax, carnuba wax, petroleum jelly, monoglycerides, diglycerides, triglycerides, cbolesterol, cholesterol esters | hexane, pentane, other aliphatic hydrocarbons, petroleum ether |
| biopolymers (collagen, polysugars, hyaluronic acid) | water, buffers | paraffin, wax, bees wax, carnuba wax, petroleum jelly, monoglycerides, diglycerides, triglycerides, cholesterol, cholesterol esters | acetone, petroleum ether |

In a preferred embodiment, the solid particles are wax particles and the polymer is both soluble in a first solvent that does not dissolve the wax particles, and is insoluble or sparingly soluble in, and precipitates from, a second solvent that dissolves the wax particles. In another embodiment, the solid particles are soluble in water-miscible organic solvents but are insoluble or sparingly soluble in water, and the polymer is soluble in water but is insoluble or sparingly soluble in and precipitates from water-miscible organic solvents. Preferred polymers for this embodiment are polyethylene glycol, polyvinyl pyrrolidone, polyvinyl alcohols, water-soluble proteins, and polysaccharides. In still another embodiment, the solid particles are soluble in water or chlorinated organic solvents but are insoluble or sparingly soluble in water-miscible organic solvents, and the polymer is soluble in water-miscible organic solvents but is insoluble in and precipitates from water or chlorinated organic solvents.

In an alternative embodiment, particles of salt can also be incorporated into the polymer/particle blend, and the salt particles can be leached out in a separate step than the step in which the solid particles are extracted. This embodiment can provide additional control of the pore size and density of the polymer matrices. Preferably, water-soluble polymers are not used in this embodiment.

In some applications, the slurry of polymer/polymer solvent/porogen is compacted into a mold before the extraction/precipitation step. The mold plays a critical role, as it allows the mixture to maintain its shape and size during the extraction/precipitation step. It is important that at least part of the mold have holes so that the porogen solvent can penetrate the mold during the extraction/precipitation step.

The mold may be made of a variety of materials, including Teflon®, high density polyethylene (HDPE), polypropylene, stainless steel (either regular or hardened), or aluminum. If the mold is made of a material other than Teflon®, it is preferable that the mold is coated with silicone, Teflon® or some other non-stick material, to aid in the removal of the polymer matrix after the extraction/precipitation step.

Figure 1B:
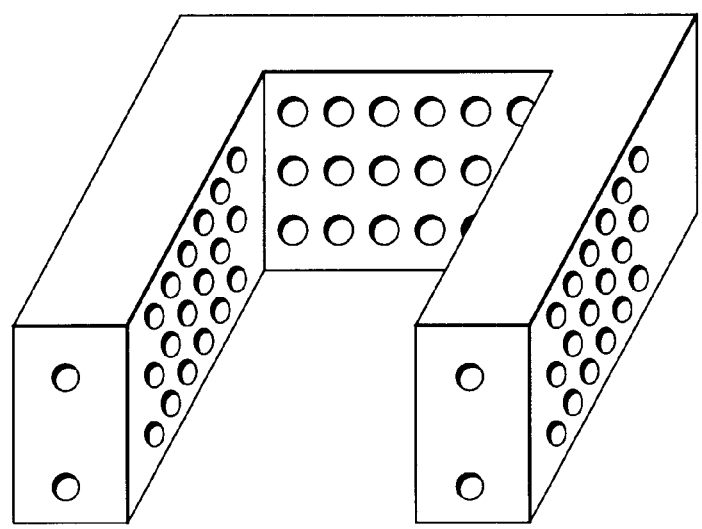
FIG. 1B is a schematic representation of the three permanently connected sides of the mold.
Figure 1C:
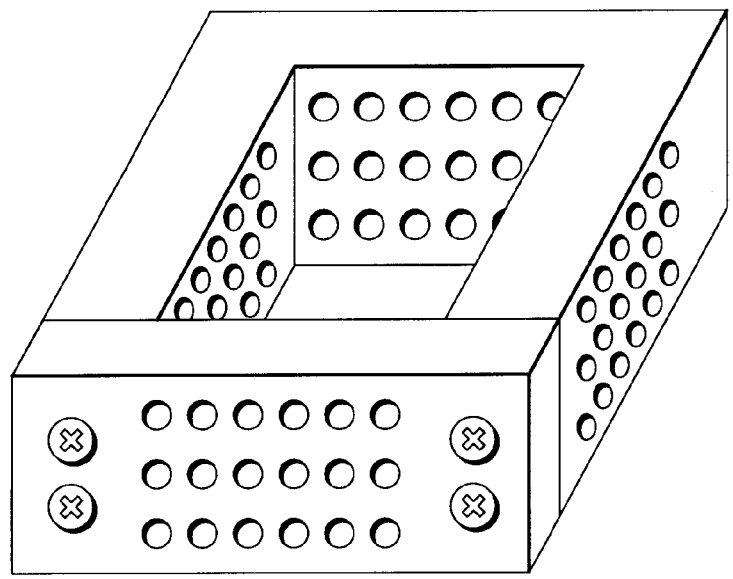
FIG. 1C is a schematic representation of four sides of the mold, with one side being connected by means of screws.
Figure 1D:
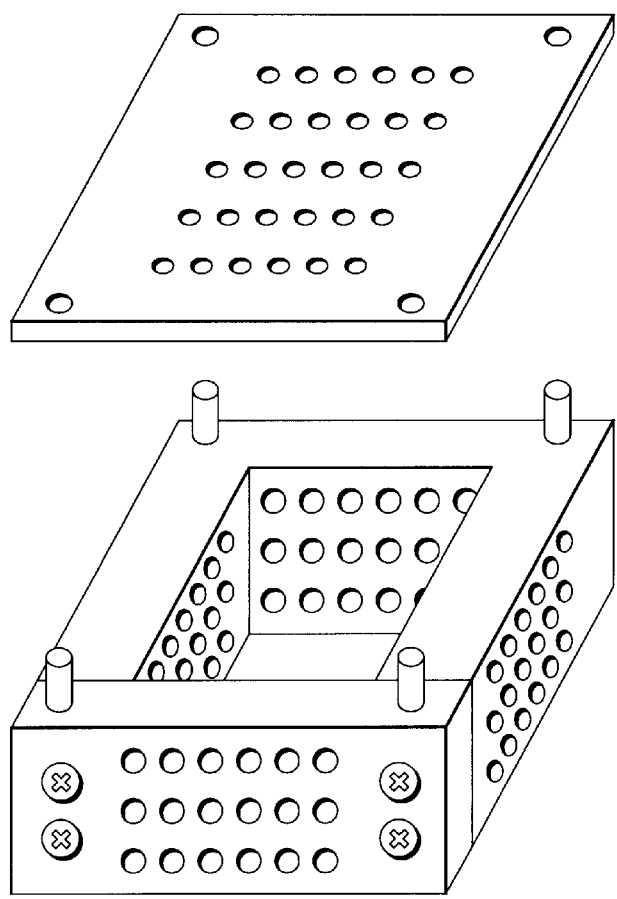
FIG. 1D is a schematic representation of the top of the mold and the sides of the mold.
Figure 1E:
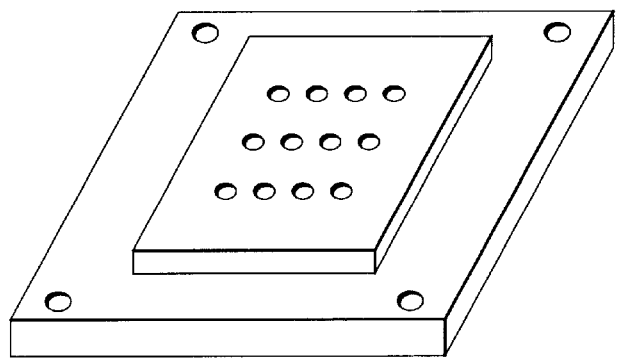
FIG. 1E is a schematic representation of the top of the mold.

An example of a mold is shown in FIGS. 1A–1E. The outer dimensions of the mold are about 1.60×1.60×1.85 cm. The mold defines an inner opening having dimensions of about 1.0×1.0×1.0 cm. The mold has six sides, each side having holes with diameters of 0.95 mm, placed 0.10 cm apart. Three sides of the mold are permanently connected, as shown in FIG. 1B. A fourth side of the mold can be attached to the three connected sides by means of screws, as shown in FIG. 1C. The top of the mold can be held in place by placing the holes in the fifth side over the guide-pins which protrude from the sides of the mold, as shown in FIG. 1D. The bottom of the mold can be held in place by placing the holes in the top over the guide-pins in the sides of the mold, as well. The top of the mold is shown in more detail in FIG. 1E.

Other molds can have a wide variety of sizes and shapes. For example, molds as large as 1.0×1.0×1.0 inch have been used to make the matrices of the invention.

Once the porous polymer matrices are formed, they can be shaped by methods known to those of skill in the art for shaping solid objects. For example, the matrices may be shaped by laser ablation, micromachining, use of a hot wire, and by CAD/CAM (computer aided design/computer aided manufacture) processes.

In one embodiment, a CAT-scan image is taken of a region of tissue and the image is digitized. This digitized image can then be used in combination with one or more techniques such as CAD/CAM or laser ablation to create a scaffold of a desired shape. This scaffold can then be used as a template for the regeneration of the desired tissue.

Complex patterns can be produced using laser ablation or laser etching to produce desired shapes. The matrix can also be formed into the desired shape by molding or by extruding. Alternatively, the matrix can be shaped by carving a finished matrix with a blade. The matrix material can be carved easily, as it is generally non-friable.

The desired shape of the matrix will depend on the particular application. For example, the matrix can be shaped into tubular structures by using a tube-shaped mold or by using a cylindrical mold, then carving out the inside of the cylinder. Tubular matrices are useful for vascular grafts and for intestinal and urethral grafts.

Properties of the Porous Polymer Matrices

Figure 2:
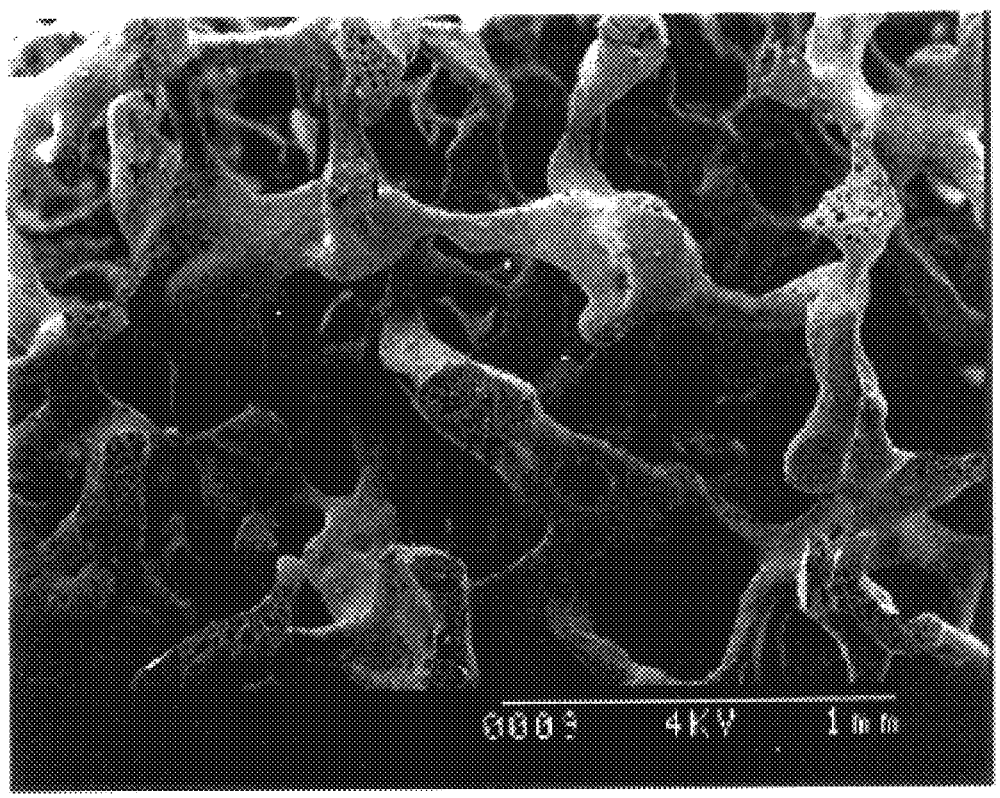
FIG. 2 is a photograph of a matrix of the invention.

The simultaneous precipitation of the polymer and extraction of the porogen, as described above, gives the polymer matrix of the invention unique properties. The matrix has a macrostructure that includes a highly interconnected, irregularly shaped porous network, as shown in FIG. 2. The porosity of the matrix allows for tissue ingrowth into the matrix, and for the matrix to dissolve as the tissue heals.

The pore size and density of the polymer matrix is controlled by adjusting the size of the solid particles, the viscosity of the polymer/particle blend, and the ratio of polymer to solid particles in the blend. The pore size is roughly the same as the size of the solid particles used to prepare the matrices, and is preferably between about 25 and 500 $\mu$m.

Figure 3A:
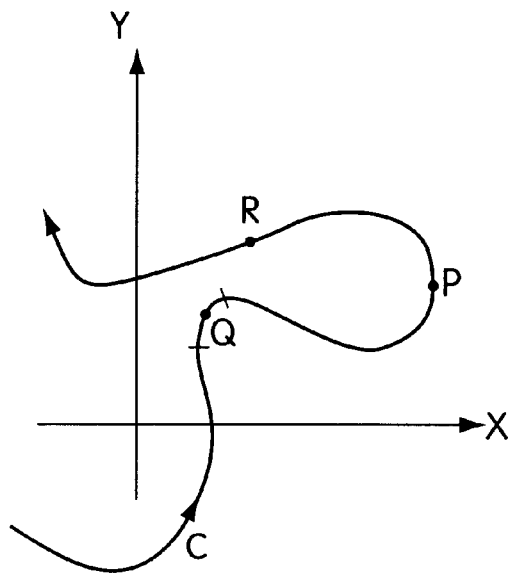
FIG. 3A is a schematic representation of a curve.

The network is generally smooth, i.e., there are very few sharp edges and few acute angles. In addition, the curvature of the network is low. Curvature is defined as follows, referring to FIGS. 3A and 3B. Curvature of a plane curve at a point C is a smooth curve lying in the (x,y)-plane; P is a point on C. The orientation of C is indicated by the arrow. At any point Q of C one can define the direction of C at Q to be the angle of the curve to the horizontal as it passes through the point Q. In FIG. 3A the angles for Q, P and R are approximately 45°, 90° and 210°, respectively. The curvature of C at P is the rate of change of this angle with respect to the distance moved along the curve from P.

In FIG. 3A, close to Q, the curve turns a full 90° over the space of about 10 mm (indicated by hatch-marks in the curve). Since the direction decreases as one moves along the curve in the positive direction, the curvature is $-90°/10$ mm=$-9$ degrees per mm;

At R, the curvature is close to 0 degrees per mm.

Figure 3B:
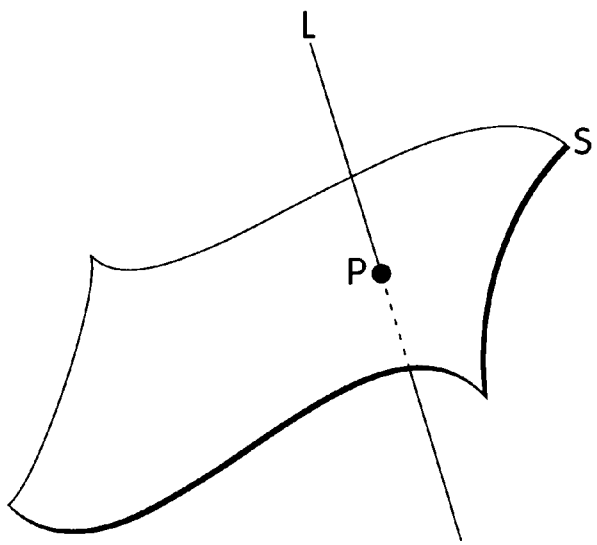
FIG. 3B is a schematic representation of a surface.

The curvature of a surface at a point is defined as follows. In FIG. 3B, S is a smooth surface, and P is a point on S. L is the straight line which passes through P and is perpendicular to the surface at P. Any flat plane containing L will intersect the surface in a smooth curve C, which passes through P, and this smooth plane curve C will have some curvature value at P, as defined above. The curvature of S is the maximal magnitude of curvature obtained and is expressed in units of degrees per unit length. Curvature is further described in Bronstein and Somendyayev, *Handbook of Mathematics* 553–554, 566–568 (1985).

Figure 4A:
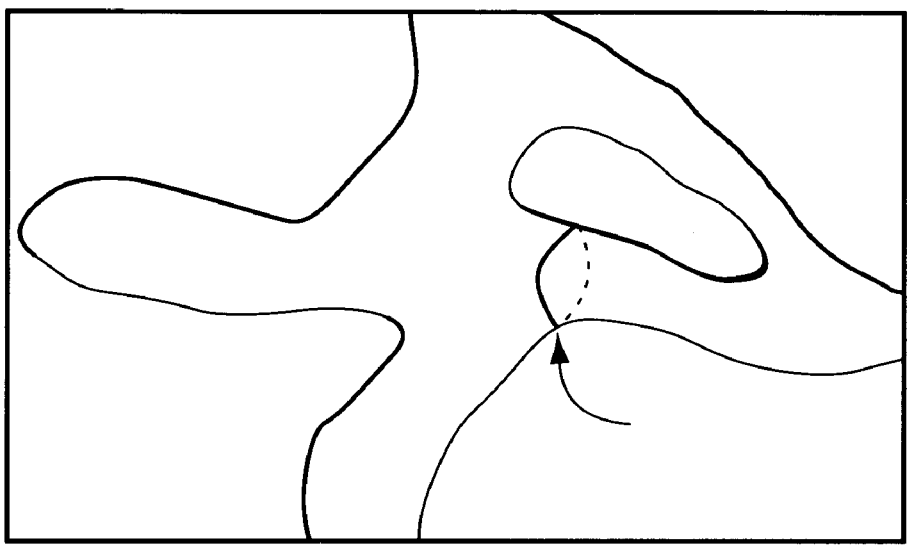
FIG. 4A is a schematic representation of the matrix of the invention showing a meridional curve.
Figure 4B:
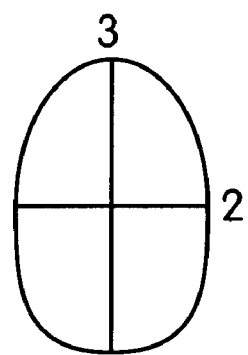
FIG. 4B is a schematic representation of a cross section of the matrix, showing the minimum and maximum diameters.

A cross-section can be drawn through a portion of the semi-solid network of the matrix by drawing a meridional curve 1 on the exterior surface of that portion, as shown in FIG. 4A. The minimum diameter 2 of a cross section is the shortest straight line that can be drawn that joins two edges of the cross-section and passes through the center of the cross-section, as shown in FIG. 4B. The maximum diameter 3 is the longest straight line that can be drawn that joins two edges of the cross-section. The diameter of a cross-section is the mean of the minimum and maximum diameters. The cross-sections of the network preferably have minimum and maximum diameters that have a ratio of 1:1 to 10:1, and more preferably have a ratio of 1:1 to 4:1, or 1:1 to 2:1; i.e., the cross-sections are roughly circular in shape.

The network is continuous, rather than being made up of discrete fibers that come into contact with each other, but are not actually connected. A line can be drawn from one point on the surface to another point without leaving the surface of the semi-solid network and without crossing a void.

The network is highly connected as well. Connectivity is determined as follows. The matrix may be "cut" in various places. For the purposes of this invention, a "cut" is defined as any cut that passes through the semi-solid network of the matrix but does not pass through a void of the matrix. The connectivity number is defined to be the number of cuts that must be made in order to guarantee that the matrix is separated into at least two disjoint pieces. A high connectivity number means that the network is connected to itself in a large number of places; this property helps the network to maintain its shape and mechanical properties.

The connectivity number must be defined in terms of the overall size and the pore size of the matrix. For example, a cubic matrix that has dimensions of about 0.5 cm on all sides and has voids defining openings with an average diameter of 50–500 $\mu$m preferably has a connectivity number of at least 10, and more preferably has a connectivity number of at least 20.

The matrix also has irregularly shaped open spaces, referred to as pores or voids, that define openings throughout the network. The ratio of the size of the voids (defined as the average of the diameters of the voids) and the size of cross-sections of the semi-solid portions (defined as the average of the diameters of the cross sections) is about 2:1 to 10:1. In general, the voids are connected, so that the matrix actually has one substantially continuous opening, rather than discrete voids. The continuity of the voids allows fluids to move throughout the matrix easily.

Figure 5A:
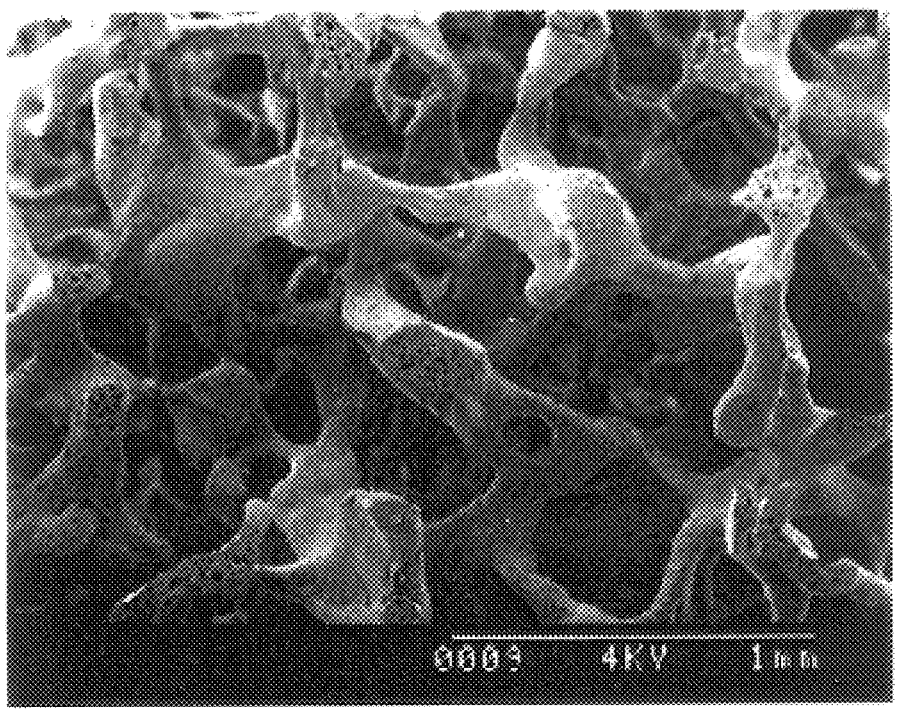
FIGS. 5A and 5B are photographs of the matrix of the invention.
Figure 5B:
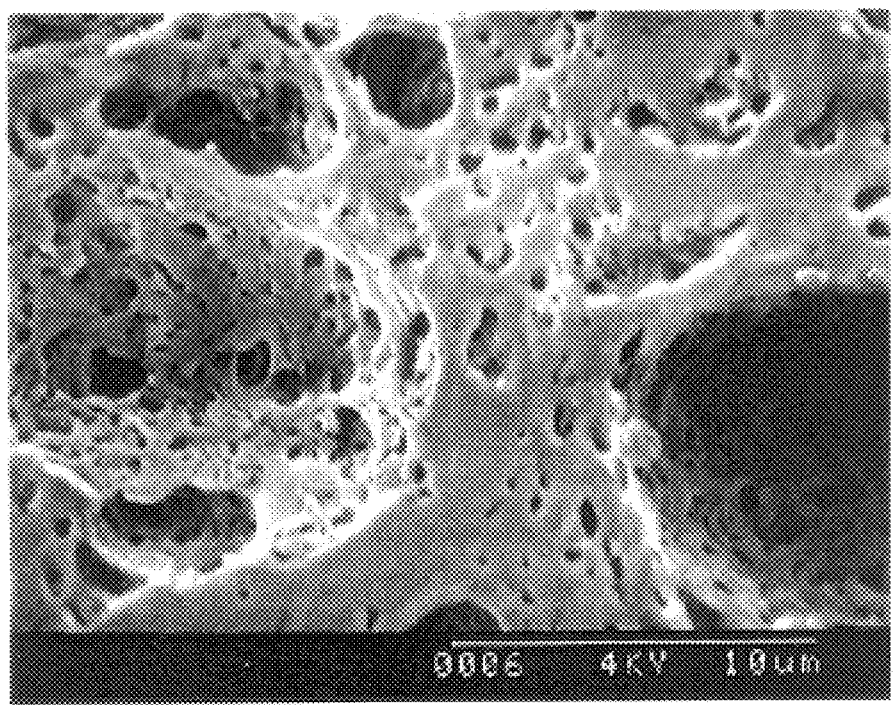

The semi-solid network of the macrostructure itself is preferably porous, as shown in FIGS. 5A and 5B. The voids contained within the network make up the microstructure of the matrix. The voids of the microstructure are different in character than the voids of the macrostructure. While the voids of the macrostructure are substantially continuous, the voids of the microstructure are not necessarily connected. In addition, the voids of the microstructure have a fractal dimension, i.e., the voids are connected to smaller voids, which are in turn connected to smaller voids.

A fractal can be constructed by using an iterative process consisting of an initiator (initial state) and a generator (iterative operation). The fractal is constructed as follows. At iteration zero, the curve is a straight line (FIG. 6A). At the first iteration, the straight line (initiator) is replaced by the generator, and the curve thus coincides with the generator (FIG. 6B). The curve has a fractal dimension of 1. At the second iteration, shown in FIG. 6C, each straight line is again replaced by the generator. The curve has a fractal dimension of 2. The third iteration (fractal dimension 3) is shown in FIG. 6D. Fractals are further described in J. Gouyet, *Physics and Fractal Structures*, ch. 1 (1996).

Although the example shown in FIGS. 6A–6D illustrates a curve with segments of equal length, the segments of a fractal do not necessarily have to be the same length for the purposes of the present invention. For bone applications, the initiator of the fractals of the invention have a length of at least 100 nm. In a preferred matrix, at least 10% of the voids of the microstructure will have a fractal dimension of at least 3, while less than 10% of the voids of the macrostructure have a fractal dimension higher than 1.

In some embodiments, the voids of the macrostructure and the microstructure are connected. These matrices are useful in applications where it is useful for the extracellular matrix to penetrate the microstructure, thus providing additional mechanical strength to the matrix. They are also useful in applications in which nutrient flow and cell migration are important. In other embodiments, the voids of the macrostructure and microstructure are not generally connected to each other; i.e., the microstructure is largely composed of discrete voids. Preferably, at least 90% of the microstructure voids are completely surrounded by macrostructure. These matrices are useful in applications where an additive is contained within the voids of the microstructure, and controlled delivery of the additive is desired.

The matrices have high degrees of porosity as well. The porosity is calculated by the following equation:

$$\text{Porosity}(P)=(1-\rho_{rel})\times 100$$

where $\rho_{rel}$ is defined as the ratio of the density of the matrix to the density of the base material (polymer). The density of the matrix is obtained by dividing the mass (grams) of the cellular material by the volume (cc or cm$^3$) of the material. (Conversion: 1 kg/m$^3$=1 mg/cc). Alternatively, the density can be determined by helium pycnometry. The matrices of the invention have porosities as high as 90%, and preferably have porosities as high as 92%, or 95%.

When conventional techniques are used to measure porosity, the matrices containing additive will in some cases have a measured porosity that is lower than a corresponding matrix made without the additive. This result is seen because the additive occupies some of the void space.

The degree to which a matrix containing an additive will have a measured porosity that is lower than the actual porosity (keeping in mind that even when additives occupy void space, the spaces are still calculated as being voids) depends on the additive used. Very dense additives with small particle sizes tend to decrease porosity less, as they do not fill much volume and in many cases are contained within the semi-solid network. Even when these additives are used, the measured porosities can be as high as 90%.

The exterior face of the matrix, i.e., the face that is adjacent to the mold wall during formation of the matrix, is porous as well; there is no "skin" covering this face of the matrix. Since the exterior face of the matrix is porous, fluids and some solids can easily penetrate the matrix. The porosity of the macrostructure of the matrix also allows for the diffusional transport of metabolites between the matrix implant and the surrounding tissue, as well as the vascularization and ingrowth of tissue.

The porous microstructure of the matrix provides an environment that is permissive to cell proliferation, cell differentiation, and deposition of an extracellular matrix. As the semi-solid portion of the matrix degrades, the voids of the porous microstructure become exposed to the mass of dividing and developing cells. The cells can then grow into the void space and produce extracellular matrix; the extra space allows the cells to develop in their natural shapes, rather than constrained shapes.

The high degree of porosity also means that the matrices have low densities. Matrices composed essentially of polymer (i.e., containing no 20 additives) have densities in the range of 0.100 g/cc to 0.700 g/cc. Preferred matrices have densities of less than 0.150 g/cc, and preferably have densities of less than 0.120 g/cc. Low densities are important for applications in which a light-weight structure is desirable. Examples include construction materials and materials used for tissue engineering.

Preparation of Porous Fibers

Porous fibers can be prepared by extruding the polymer/polymer solvent/porogen slurry into hexane. For example, the slurry can be loaded into a syringe and injected into a container of hexane, or some other porogen solvent. As the slurry comes into contact with the hexane, the polymer precipitates and forms a fiber.

Due to the extrusion process, the pores of the fiber are elongated and oriented in the same direction, i.e., in the longitudinal direction of the fiber. This orientation is useful in applications such as cardiac tissue repair, muscle repair, and tendon repair.

Preferred polymers for preparing porous fibers, and, particularly, porous sutures, are biodegradable polymers such as polylactide, polyglycolide, polyorthoesters, poly (ester amides), polyanhydrides, polydioxanones, polycarbonates, and copolymers and blends thereof.

Methods for Preparing Blends

Matrices containing blends of polymers are prepared using a variation of the method described above. The polymers are combined before the polymer solvent is added. A polymer solvent that dissolves both polymers is used. For example, when PLA, PGA, PLGA, PEG, and poloxamers are used to make blends, methylene chloride, chloroform, acetone, dimethylformamide, dimethyl sulfoxide, dioxane, N-methyl pyrrolidine, or hexafluoroisopropanol can be used as the solvent. In addition, solvent mixtures of water/acetone, acetone/dimethyl sulfoxide, acetone/dimethylformamide, and acetone/dioxane can be used.

Properties of Polymer Blend Matrices

One advantage of using polymer blends is that properties, such as mechanical strength and degradation rate, can be controlled by altering the ratio of the polymers in the blend. Particularly useful blends include those of water insoluble polymers and water soluble polymers. The mechanical properties and degradation rates of the matrices can be controlled, independently of porosity, by altering the relative amounts of the two different polymers; matrices that contain higher relative amounts of water soluble polymers will degrade faster than matrices containing lower amounts of water soluble polymers.

Examples of water soluble polymers that can be used include PEO, PEG, PVA, the polymers described in Hubbell et al., U.S. Pat. Nos. 5,626,863; 5,567,440; and 5,567,435, and di- and triblock copolymers of polypropylene oxide and polyethylene oxide, generically referred to as poloxamers (available from BASF under the trade name Pluronics®). These water soluble polymers can be blended with water insoluble polymers such as PLA, PGA, PLGA, PLLGA, PCL, polycarbonate, polyethers, polyesters, and polyamides.

Thus, the degradation rate of a matrix can be fine-tuned using the methods of the invention. The degradation rate is important for many applications. For example, if the matrix degrades too quickly, the cells will not have proper support on which to grow. If the matrix degrades too slowly, the cells will not have enough room to grow or to produce extracellular matrix. Thus, the cells will either not multiply, or will develop with strained shapes. Matrices that degrade at the same rate that tissue ingrows into the matrix, or that tissue remodeling occurs within the matrix, can be prepared.

The degradation rate can also be controlled by altering the porosity of the matrix, since matrices with higher porosities generally have faster degradation rates. In many applications, however, it is advantageous to be able to alter the degradation rate without altering the porosity. Such applications include tissue engineering and scaffold based drug delivery, including applications in which the scaffold contains microspheres. The present invention thus provides a way to alter degradation rates without altering the porosities of the matrices.

Matrices with different mechanical properties are useful in different applications. Matrices that can withstand stress without compressing are useful in applications such as muscular and skeletal reconstruction, while matrices that compress relatively easily without breaking, and are able to return to their original size and shape, are useful in a wide variety of applications, such as cartilage repair.

The matrices can also contain blends of conductive polymers such as polypyrrole, polyaniline, polyacetylene, polythiophene. The resulting matrices will be conductive as well, and can be used in applications such as chromatography, EM shielding, electronics packaging, and fuel cells.

Materials to be Incorporated into the Polymer Matrices

Various materials can be incorporated into the polymer matrices. These materials can be incorporated when the matrices are formed, or after the matrices are formed.

For example, catalysts can be incorporated into the polymer matrices. These catalysts can be organic catalysts, such as enzymes and porphyrin catalysts, inorganic industrial catalysts, such as zeolites and other Lewis acids, or organometallic catalysts. Exemplary enzymes include glucose oxidase, heparinase, proteases, and horseradish peroxidase. Exemplary inorganic and organometallic catalysts include zeolites, silica, alumina, oxidizing agents, reducing agents, Zeigler Natta catalysts, aluminum catalysts, nickel catalysts, and zinc catalysts.

Incorporation of the catalysts in polymer matrices allows them to be readily removed and reused in industrial processes, such as cracking, hydrocracking, hydrogenation, and polymerization.

Various cells can be seeded or adsorbed onto the porous matrices after the matrices are formed to form artificial organs. For example, skin cells, such as keratinocytes, can be seeded into the matrix for use as artificial skin. Cells from various parenchymal tissues or organs can be seeded into the matrix to form tissue equivalents with the metabolic functions(s) of the tissue from which the cells were derived. Chondrocytes can be seeded into the matrix to form ears, noses, and other cartilaginous body parts.

The list of cells that can be grown on the matrices of the invention also includes bone marrow cells, periosteal cells, smooth muscle cells, endothelial cells, fibroblasts, epithelial cells, tenocytes, neuronal cells, neuronal support cells (e.g., Schwann cells), hepatocytes, liver cells (e.g., Kupffer cells and fibroblasts), pancreatic islet cells, and cardiac myocytes.

Other therapeutic agents can be incorporated into the matrices as well. The matrices can then be used for local or systemic delivery of the incorporated agents following administration to a patient. Examples of therapeutic agents include synthetic inorganic and organic compounds, proteins (the term protein refers to both.proteins, which have at least 100 amino acid residues, and peptides, which have less than 100 amino acid residues), polysaccharides and other sugars, lipids, genetic materials that induce cell growth, cell migration, cell division, cell differentiation, and tissue growth, ribozymes and ribozyme guide sequences, and nucleic acid molecules having therapeutic, prophylactic or diagnostic activities. Nucleic acid molecules include genes, plasmid DNA, naked DNA, and antisense molecules which bind to complementary DNA to inhibit transcription.

Other bioactive or therapeutic agents include vasoactive agents, neuroactive agents, hormones, growth factors, cytokines, anaesthetics, steroids, anticoagulants, anti-inflammatories, immunomodulating agents, cytotoxic agents, prophylactic agents, antibiotics, antivirals, antigens, and antibodies. In some instances, antibodies or antigens would otherwise have to be administered by injection to elicit an appropriate response.

Other pharmaceutical compounds can also be incorporated into the matrix of the invention. The controlled degradation of the matrix allows for controlled release of the pharmaceutical agents, while the incorporation of the agent into the matrix allows for localized delivery. For example, antibiotics such as gentamycin, vancomycin, erythromycin, and safromycin can be used to treat local infections. These agents are particularly useful in treating bone infections (osteomyelitis) and in spinal fusion procedures. The analgesics lidocaine, bupivacaine, prilocaine, and procaine can be incorporated into matrices and used for local pain management. These agents are particularly useful in spinal fusion, and in bone and cartilage repair. Glucocorticoids, hydrocortisone, and other non-steroidal anti-inflammatory drugs can be incorporated into the matrices and placed in the body to treat local inflammation, especially inflammation resulting from bone repair or spinal fusion. Hormones can also be incorporated.

In some embodiments, the bioactive agents are contained in microspheres composed of, e.g., PGA, PLA, PLGA, PCL, di- and triblock copolymers of polypropylene oxide and polyethylene oxide, collagen, ethyl cellulose, carboxymethyl cellulose, or gelatin. The polymeric gel materials described in Hubbell et al., U.S. Pat. Nos. 5,573,934, 5,529,914, 5,380,536, and 5,232,984 can be used as well. In other embodiments, the bioactive agents are contained in microcapsules made of, e.g., polyamide or polyesters. The microspheres serve the dual purpose of protecting sensitive bioactive agents during the preparation of the polymer matrices and further controlling the release rate of the agents contained within the microspheres or microcapsules. Compounds with a wide range of molecular weight, for example, between 10 and 500,000 grams per mole, can be encapsulated.

Any biocompatible or pharmacologically acceptable gas can be incorporated into the particles or trapped in the pores of the particles using technology known to those skilled in the art. The term gas refers to any compound which is a gas or capable of forming a gas at the temperature at which the matrix is used. In one embodiment, retention of gas in the porous matrices is improved by forming a gas-impermeable barrier around the porous matrix. Such barriers are well known to those of skill in the art.

The matrices of the invention can also be used to deliver contrast agents to specific sites. For example, oxytetracycline (OTC) can be incorporated into a matrix and placed in the body to aid in bone imaging. Radioactive agents can be incorporated as well. Matrices including these agents are useful for local tissue irradiation.

Other imaging agents which may be utilized include commercially available agents used in positron emission tomography (PET), computer assisted tomography (CAT), single photon emission computerized tomography, x-ray, fluoroscopy, and magnetic resonance imaging (MRI).

Examples of suitable materials for use as contrast agents in MRI include the gadolinium chelates diethylene triamine pentacetic acid (DTPA) and gadopentotate, dimeglumine, iron, magnesium, manganese, copper, and chromium.

Examples of materials useful for CAT and x-rays include iodine based materials for intravenous administration, such as the ionic monomers diatrizoate and iothalamate, the non-ionic monomers iopamidol, isohexol, and ioversol, the non-ionic dimers iotrol and iodixanol, and the ionic dimer ioxagalte. The contrast or diagnostic agents can be detected using standard techniques available in the art and commercially available equipment.

Additives can be incorporated into the semi-solid network to change the properties of the matrix. For example, the additives can make the matrix stronger, more flexible, or electrically conductive. Matrices including graphite, metal powders, glass fibers, or glass beads are useful as structural composites for the construction of specialty packaging. Matrices including carbon powder, graphite powder, graphite fibers, metal powders, or metal fibers are useful as porous electrodes and/or solid state electrolytes for battery and fuel cell applications, as well as for electromagnetic (EM) shielding.

When inorganic salts such as transition metal sulfates, carbonates, phosphates, nitrates, and sodium salts, are used as additives, the resulting matrices are useful in the production of porous ceramics. When other inorganic salts, for example, calcium carbonate, β-glycerophosphate, calcium phosphate, sodium carbonate, sodium phosphate, and large particulate hydroxyapatite, are incorporated, the resulting matrices are useful for the fabrication of osteoconductive, osteoinductive, chondroconductive, and chondroinductive scaffolds for bone and cartilage tissue engineering.

The additives polyethylene, polypropylene, Teflon®, nylon powder, and nylon particles can be incorporated as well. The resulting matrices are useful as structural composites for the construction of specialty packaging.

Polymer fibers (e.g., polyethylene, polypropylene, Teflon®, PGA, or nylon fibers) can be added to the matrices to provide mechanical strength and/or to alter the degradation rate of the matrix. The matrices prepared with these additives can be used as structural composites for construction or for tissue engineering.

Methods for Incorporating Additives

Matrices in which additives are incorporated into the semi-solid network are prepared using a variation of the general method described above. Preferably, the agent is incorporated into the polymer matrix by mixing particles, solutions, or suspensions of the agent with the polymer/porogen blend. This method of incorporating the agent is suitable for those agents which are not denatured when placed in contact with the polymer solvent or the porogen solvent. The additives can be contained in the semi-solid network, in the pores of the macrostructure, or in the pores of the microstructure.

Matrices in which the additive is incorporated into the voids of the microstructure are prepared by first incorporating the additive into the porogen material. The porogen is dissolved in a suitable solvent, and the additive is added. The mixture is stirred to distribute the additive evenly; the solvent is then allowed to evaporate. The porogen material is cryo-milled, as described above. The matrix is then prepared using the procedure described above. An excess of additive can be used in cases where some of the additive is washed out of the matrix during the porogen extraction steps.

The agents can also be incorporated in microparticles, preferably microparticles prepared from water-soluble polymers, which can be incorporated into the polymer matrix.

Materials can also be incorporated into the porous polymer matrices after the matrices have been prepared. In one embodiment, the matrices can be seeded with cells after the matrices are formed. In another embodiment, diagnostic or therapeutic agents can be incorporated into the polymer matrices by adsorption or absorption after the matrices are prepared.

When agents are incorporated into the polymer matrix by absorption or adsorption after the polymer matrix is prepared, a solution containing an agent to be incorporated should be prepared using a solvent that is a non-solvent for the polymer. The agent can then be adsorbed or absorbed onto the matrix.

Methods in which the additive is contained in a microparticle, or is incorporated into the polymer matrix by after the polymer matrix is prepared, are useful in those embodiments in which the agent can be denatured or otherwise suffer a loss of activity during preparation of the polymer matrices.

Those of skill in the art can readily determine an appropriate amount of incorporated agents. The amount of agents to be incorporated will depend on several factors, including the types of polymers used, the porosity of the matrix, the type of agent to be delivered and the age and body weight of the patient.

Titanium, which provides mechanical strength, can be combined with the matrices in a number of ways. Titanium fibers, titanium powders, or titanium dioxide can be incorporated into the semi-solid network, and the network can then be cured. For example, a matrix with titanium dioxide incorporated into the semi-solid network can be cured in a reducing environment (e.g., in the presence of $H_2$). Matrices including these materials are useful in applications such as spinal fusion (spinal cages).

Alternatively, a slurry of polymer/polymer solvent/porogen can be poured or pressed into a titanium spinal cage or a titanium mesh. The entire assembly can then be subjected to the extraction procedure; the result is a titanium cage containing the matrix within the cage or a titanium mesh filled with the matrix. The titanium provides mechanical strength, while the matrix acts as a drug-delivery device and as a scaffold to support cell growth and differentiation.

In yet another method, a matrix with a macrostructure having pore sizes of at least 3 mm to 1 cm, and having a reducing agent incorporated, is prepared. This mesh is plated with titanium using, for example, electrode-less plating techniques. The entire assembly is sintered, causing the polymer macrostructure to disintegrate, leaving a porous titanium macrostructure. The porous titanium structure can then be packed again with a porous polymer matrix that provides a suitable environment for cell and tissue growth, as described above.

Inorganic and organic reducing agents can be included in the matrices as well. When these agents are incorporated into the matrices, metals can be plated (through electrodeless plating) or deposited on the matrices by exposing the matrices to solutions of metal salts such as palladium sulfate, copper sulfate, nickel sulfate, or other metal sulfates under conditions where the metal will precipitate onto the matrix. The coated matrices can be used as high surface area solid supports for catalysis, light weight electrodes for batteries, fuel cells, and as other battery and electronic components.

Methods for Altering Surface Properties

The surface properties of the matrices can be altered by coating the matrices. For example, the matrices can be soaked in solutions containing hydrophilic natural or synthetic materials. The matrices can be soaked in natural polymers such as collagen, hyaluronic acid, extracellular matrix proteins (e.g., fibronectin, vitronectin, and laminin), bone morphogenetic protein (BMP), and other growth factors, synthetic materials such as PEG, PEO, hydrogels, and carboxylic acid-containing substances. The matrices can also be soaked in acidic or basic solutions. After the matrices are soaked, they can be lyophilized. The coatings can be used to improve the wettability of the matrices and/or modify the surfaces of the matrices to enhance cell attachment, migration, and differentiation. Fatty acid esters can be used to make the surfaces of the matrices more erodible.

Alternatively, the surfaces of the matrices can be altered by modifications such as the attachment of hydrophilic groups to the surface layers of the polymers. These techniques can make the surfaces of the matrices more wettable; they can also make the matrices better environments for cell growth and development.

Preparation of Insoluble Polymer Matrices

Polymer matrices composed entirely of polymers such as high density polyethylene (HDPE) or polypropylene, which are soluble only in boiling aromatic hydrocarbons, can be prepared using a variation of the method described above. These polymers are referred to herein as "insoluble polymers."

A polymer (the "carrier polymer") (e.g., PMMA or polystyrene) is dissolved in a polymer solvent, as described above. The insoluble polymer is introduced into the carrier polymer phase as a powder or as microparticles. The porogen (e.g., paraffin, wax, or bees wax) is added as well, and the combination is mixed to form a slurry, as described above. The matrix is molded, as described above. The porogen is then extracted with concurrent precipitation of the carrier polymer phase to yield a composite composed essentially of carrier polymer and insoluble polymer. The composite is then annealed at a temperature higher than the glass transition temperature of the insoluble polymer, but below the melting temperature of the carrier polymer. The particulate insoluble polymer fuses to yield a continuous phase of the insoluble polymer. The carrier polymer is then extracted to yield a porous network of the insoluble polymer (as the insoluble polymer is insoluble in most solvents, a wide variety of solvents can be used). The result is a porous polymer matrix composed essentially of the insoluble polymer.

In a variation of this approach, an inorganic material is used in combination with the carrier polymer phase. When this material is sintered in the final step, a highly porous ceramic network is obtained. This approach is useful in the production of highly porous hydroxyapatite, other ceramics, or semiconductors.

Preparation of Multi-layer Matrices

Matrices can be prepared using a polymer such as PLA with a photo-initiator such as methyl methacrylate incorporated into the polymer. The matrices are prepared in layers. A thin layer of polymer/polymer solvent/porogen slurry is placed on a surface. The layer is then exposed to an ultraviolet light source to initiate cross-linking of the polymer. A new layer of the slurry is placed on the first layer; this layer is then exposed to the light source as well. The process is continued until a matrix of the desired thickness is obtained. The porogen is then extracted from the matrix, as described above. This method can be used to prepare both interpenetrating networks and semi-interpenetrating networks.

Alternatively, stereospecific curing can be used to create different shapes of cross-linked polymer in the matrix. For example, stereospecific curing can be used to create columns of cross-linked polymer within a matrix.

Matrices can be prepared in which layers of cross-linked polymers are sandwiched between layers of non-cross-linked polymers. The cross-linked and non-cross-linked layers are connected with thin layers of a polymer that will cross-link to both layers, thus holding the layers together. The cross-linked layers are relatively stiff, while the non-cross-linked layers are flexible. Thus, these matrices are useful in applications where the matrix is required to be strong, yet be able to provide cushioning. An example is joint repair.

Additional layered composites can be formed by laminating two matrices having different properties; the matrices can be laminated, for example, by solvent welding. A matrix having an average pore size of less than 50 $\mu$m can be laminated to a matrix having an average pore size of greater than 100 $\mu$m. Alternatively, such a composite could be formed by layering polymer/porogen slurries with different sized porogens before extraction.

Bi-layered matrices prepared by these methods are useful in applications where it is desirable to prevent tissue ingrowth for some period of time.

Use

Various articles of manufacture can be prepared using the methods and compositions of the invention. These articles include matrices to support cells for cell growth and tissue engineering, drug delivery devices, fuel cells, tubular porous structures, porous fibers, and biodegradable and non-biodegradable foams and packaging materials.

For tissue engineering applications, the preferred pore size is between 1 $\mu$m and 600 $\mu$m, and the preferred density of the polymer matrix is between about 0.100 g/cc and 0.200 g/cc. The pore size ensures that cells or tissue incorporated into the polymer matrix have adequate access to nutrients. Bioactive agents, such as growth factors, nutrients, and genetic material, can be incorporated into the polymer matrix to facilitate growth, differentiation, and/or function of the incorporated cells or tissue. One of skill in the art can readily determine an appropriate type and amount of growth factor, nutrient, or genetic material for a particular cell type.

The porous macrostructure has a high surface area to weight ratio, thus providing an environment conducive to colonization by cells. As the semi-solid portion of the matrix degrades, the voids of the porous microstructure become available to the mass of dividing and developing cells. In addition, the porous microstructure of the matrices allows for high nutrient exchange.

The highly interconnected structure of the matrix (i.e., the high connectivity number) provides it with mechanical strength, enabling the network to maintain its original shape and size for an appropriate period, even when cells are added and/or the matrix is present in the body. This is advantageous, as the size of the resulting tissue will be substantially the same size as the polymer matrix.

Cells and/or tissue can be incorporated into the polymer matrices, for example, by seeding the matrices with cells. Such polymer matrices can be used to grow tissue in various shapes. For example, artificial cartilage can be formed into the shape of a nose or ear. Artificial organs can be prepared using cells from the desired organ. Artificial skin can be prepared using cells from the dermis and/or epidermis.

Porous matrices prepared from biodegradable polymers can be prepared and used as biodegradable foams. Such foams can be used, for example, in tissue engineering and tissue augmentation applications. Polymers useful for these applications include polyhydroxy acids, such as PLA, PGA, PLGA, polyorthoesters, poly(ester amides), polyanhydrides, polydioxanones, polycarbonates, cellulose, modified cellulose (cellulose esters and ethers), and copolymers and blends thereof.

The site, or sites, where the matrix is to be implanted is determined based on individual need, as is the requisite number of molecules or cells. For cells having organ function, for example, hepatocytes or islet cells, the matrix can be implanted into the mesentery, subcutaneous tissue, retroperitoneum, properitoneal space, and intramuscular space. For formation of cartilage, the matrix can be implanted into the site where cartilage formation is desired.

Biodegradable matrices can be used to treat bone fractures, since the matrices can provide sufficient strength to permit fixation and good tissue/material compatibility. In addition, the matrices can be easily molded, into potentially complex shapes, for easy placement. The controlled degradation of the polymers permits good tissue integration and optimum bone function upon healing. These materials can reestablish the mechanical integrity of the bone, then subsequently degrade to allow new bone formation. Many of the metallic orthopedic devices currently in use shield stress during healing and can lead to bone atrophy.

Bone grafts can be prepared by preparing tubular polymer matrices. The tubes can be prepared with a suitable shape and thickness to support the bone and allow bone to grow through the matrix. Preferred polymers for this application are biodegradable polymers such as PLA, PGA, polyanhydrides, polyorthoesters, polydioxanones, poly (amide esters), polyiminocarbonates, polycarbonates, poly (meth)acrylates such as PMMA, and copolymers and blends thereof. Preferably, ceramics such as hydroxyapatite or other osteoinductive and osteoconductive insoluble materials are added to the bone grafts. Those of skill in the art can readily determine an appropriate amount of these materials to include in the polymer matrix.

The matrix can also be implanted as a bulking agent for hard tissue defects, such as bone or cartilage defects, congenital or acquired disease states, or defects resulting from secondary trauma or burns. For example, a matrix can be implanted into the area surrounding the skull where a bony deformity exists.

The polymer matrices can be formed into the shape of an implant that serves a mechanical function. Examples of such implants include rods, pins, screws, plates, and anatomical shapes.

Cylindrical polymer matrices with holes in the center and/or channels through the matrices can also be used to prepare vascular grafts and other hollow tubes. The tubes can be seeded with cells to form vascular grafts, bone grafts, ureters, and intestine. Preferred polymers for this application include polyhydroxy acids such as polylactic acid, polyglycolic acid, and copolymers thereof, and also include copolymers and blends with water-soluble polymers such as polyethylene glycol, polyethylene oxide and polyvinyl alcohol.

The matrices of the invention can also be used in controlled-release delivery systems. Matrices made of PLA, PGA, PLGA, PEG, PEO, and blends thereof are preferred for these release systems. The additives to be released are incorporated into the semi-solid network and the voids of the microstructure, preferably during formation of the matrix. Although most of the additive is contained within the microstructure, a portion of some of the particles may protrude into the voids of the macrostructure. In these cases, the entire particle is calculated as being contained within the microstructure. Typically, the polymer matrices will include between about 0.01% (w/w) and 90% (w/w) of additive.

The additive can be incorporated in either the semi-solid network or the voids of the microstructure for slow, controlled delivery. As the matrix dissolves, the additive trapped in the voids of the microstructure or the semi-solid network is released. The additive can be incorporated into the voids of the macrostructure when it is desirable to release the additive soon after the matrix is placed in growth medium or in the human body.

In other embodiments, the bioactive agent-containing matrix can be ground or cut into smaller pieces; for example, the matrix can be ground into 1–2 mm particles. Preferably, the matrix is ground in a refrigerated grinder. These particles can be used in the same ways that microspheres are used. The particles can be combined with a suitable solvent or liquid phase to form a slurry or gelable slurry. This slurry can then be injected into a body or applied directly to a site of bone or tissue repair. The advantage of the slurry is that it can be molded into a desired shape and size at the time of application. The slurry can form a coating on the surface of infected bone, and can deliver antibiotics or growth factors to that site.

The particles can incorporate small and large drugs, and can release the incorporated drugs over time periods ranging from hours to months. Because the particles can be extremely porous, they can deliver incorporated therapeutic agents at relatively fast rates, compared to other delivery devices. Water-soluble polymers are particularly preferred for use in this application, because the porous matrix rapidly dissolves following administration. Polyethylene glycol is the most preferred water-soluble polymer.

When injected, the porous polymer particles can be administered in a pharmaceutically acceptable carrier. Similarly, when used in inhalation therapy, the particles can be mixed with a suitable carrier for administration via pulmonary delivery. Those of skill in the art can readily determine an appropriate carrier for these modes of administration. When used for injectable or inhalable delivery devices, the matrices can be formed into particles or microparticles, with a size between 1 and 200 $\mu$m, for example, by laser ablation or micromachining.

A therapeutically or diagnostically effective amount of the agents is incorporated into the polymeric matrix. An effective amount can be readily determined by a person of ordinary skill in the art, taking into consideration factors such as body weight, age, physical condition, the therapeutic or diagnostic goal desired, the type of agent used, the type of polymer used, the initial burst and subsequent release levels desired, and the desired release rate.

The matrices of the invention can be placed in a number of sites in the human body, or an animal body. Matrices can be placed in an open surgical site, for example, in the case of bone repair or tissue replacement. Alternatively, they can be placed subdermally. Subdermal placement is useful for the controlled delivery of hormones such as estrogen. Thin sheets or liquid slurries of the matrices can be placed in the tooth pocket to deliver periodontal disease-fighting drugs, as well as to control local pain.

The materials of the invention can be used in many applications requiring load-bearing capacities and controlled degradation. In a preferred embodiment, the compression modulus of the polymer matrices is on the order of about 0.4 MPa at 4% strain.

The polymer matrices can be combined with fillers, reinforcement materials, excipients, or other materials as needed for a particular application. Examples of fillers include calcium-sodium-metaphosphate, as described in U.S. Pat. No. 5,108,755, which is incorporated herein by reference. Those of skill in the art can readily determine a suitable amount of these materials to include in the matrix.

The porous polymer matrices can also be used as fuel cells. In one embodiment, the matrices are used to prepare porous electrodes, and to incorporate solid electrolytes. Suitable electrolytes include polypyrrole, polystyrene sulfonate, sulfonated elastomers, poly(meth)acrylic acid, and other conducting polymers known to those of skill in the art. Alternatively, metals can be plated on porous polymer matrices to form porous electrodes using techniques well known to those of skill in the art. For example, the oxidation of $Ag(NH_3)^{2+}$ to metallic silver in the presence of aldehydes (the Tollen's test) can be used to plate porous electrodes with silver. Electrodes prepared using the disclosed methodology are significantly less dense than conventional electrodes.

Solid supports prepared using the matrices can be used in solid phase peptide syntheses and oligonucleotide syntheses, and other applications which involve the use of solid phase supports. Preferred polymers for this embodiment are insoluble or sparingly soluble under the proposed conditions of use.

As described above, porous fibers can be prepared by preparing a blend of a polymer and a solid particle in an appropriate polymer solvent, shaping, extruding or spinning the blend into a fiber, and extracting the particles in an appropriate solvent. The fibers can be used for a variety of purposes, for example, as sutures, fibers, artificial tendons, and porous filaments. Additionally, the fibers can be woven together to form high strength, low weight materials.

The materials of the invention can also be used to prepare biodegradable packing materials. Cellulose and modified cellulose are preferred polymers for such applications. Similarly, foams of non-biodegradable polymers, for example, polystyrene, polymethacrylate, polyethylene, polypropylene, and other relatively inexpensive polymers, can be prepared. Such foams can be used for packaging and for other shock absorbing applications.

The porous matrices can be designed to have high structural strength and low density. Such matrices can be used as lightweight structural materials. For example, the matrices can be used to prepare building materials, to prepare structural components for boats, automobiles, bicycles, airplanes, and vehicles designed to go into space, and for other structural uses. Preferred polymers for these uses are non-degradable, and have high strength. For example, a porous tubular structure with an outer non-porous tubular laminate can be used as a lightweight material. Polyvinyl chloride is especially suitable for this application.

The following examples are set forth in order to illustrate the invention. They are not meant to be construed as limiting.

EXAMPLE 1

Preparation of the Polymer Matrix A 1.0×1.0×1.0 cm matrix was prepared as follows. First, a Teflon® mold having outer dimensions of about 1.60×1.60×1.85 cm and having inner dimensions of about 1.0×1.0×1.0 cm, as shown in FIGS. 1A–1E, was assembled. The mold had six sides, each side having holes with a diameter of 0.95 mm, placed 0.10 cm apart. One side of the mold was attached to the three connected sides by means of screws, as shown in FIG. 1C. A fifth side was attached by placing the holes in the piece over the guide-pins, as shown in FIG. 1D. Scotch®-brand adhesive tape was placed over the holes on all five sides.

Poly(lactic acid-co-glycolic acid) (PLGA) was ground to a fine powder using a refrigerated grinder. Liquid nitrogen was added, as needed, during grinding to maintain the PLGA in a solid form.

Paraffin (Fisher Chemicals) was ground using the same procedure. The paraffin particles were then sieved through a series of meshes.

Figure 7:
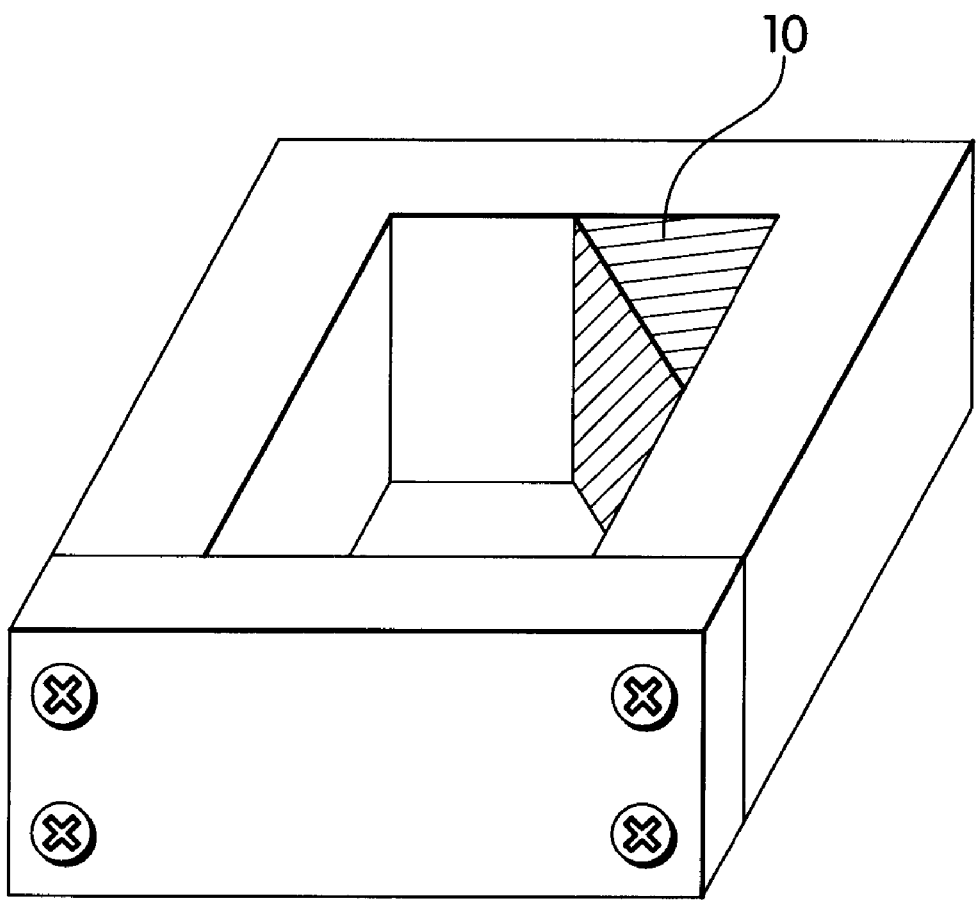
FIG. 7 is a schematic representation of a partly filled mold.

200 mg of the PLGA was placed on a watch glass. 1–2 mL methylene chloride was added, and the resulting mixture was stirred for about 1–2 minutes with a metal spatula to form a viscous paste. 400 mg of 500–425 µm paraffin particles and 400 mg 300–425 µm paraffin particles were added to the paste. Methylene chloride was added as needed, in aliquots of about 0.5 mL, to maintain the consistency of a thick paste. When a relatively homogenous mixture was obtained, the mixture was packed into the mold. In order to avoid the formation of air bubbles, one corner of the mold was packed with the mixture 10 first, as shown in FIG. 7. The rest of the mold was then filled with the mixture.

The sixth side of the mold was placed over the guide pins and pressed firmly against the frame of the mold. The mold was then placed in a 150 mL beaker containing 100 mL hexane. The porogen was extracted by leaving the mold in boiling hexane for 2 minutes. After this time, the mold was removed from the hexane, and the adhesive tape was removed. The mold was then placed in boiling hexane for an additional 13 minutes to extract more of the porogen.

The mold was then removed from the hexane. The top of the mold was removed, and the mold was placed in a 150 mL beaker containing 100 mL of fresh hexane. The mold was kept in boiling hexane for 15 minutes to extract more of the porogen.

The mold was then removed from the hexane, and the matrix was carefully removed from the mold. The porogen was then extracted in fresh hexane (boiling) for 15 minutes. After this time, the matrix was removed from the hexane; the remaining porogen was extracted in 100 mL fresh hexane (boiling) for an additional 15 minutes.

The matrix was air-dried (using house air), then lyophilized for 24 hours, to remove any remaining polymer solvent and porogen solvent. The density of the finished matrix was 120–150 mg/cc.

In separate experiments, 200 mg of PLA or PLGA or PMMA was dissolved in 2–3 ml methylene chloride or chloroform. After the polymer was completely dissolved (as determined by lack of any particulates) 800 mg of paraffin particles with a size ranging from 500–300 gm were mixed in with a spatula to yield a putty including the polymer, paraffin and solvent. This mixture was then compacted into a 1 cubic centimeter Teflon® mold and placed in a beaker containing 60 ml of warm hexane for extraction of the paraffin. After 15 minutes, the mold was dismantled and the porous polymeric cube was released. The cube was then further subjected to two separate extractions of 15 minutes each in warm hexane to remove any residual traces of paraffin. The resulting porous polymeric cubes had a porosity greater than 85%.

EXAMPLE 2

Measurement of Residual Paraffin

Figure 8:
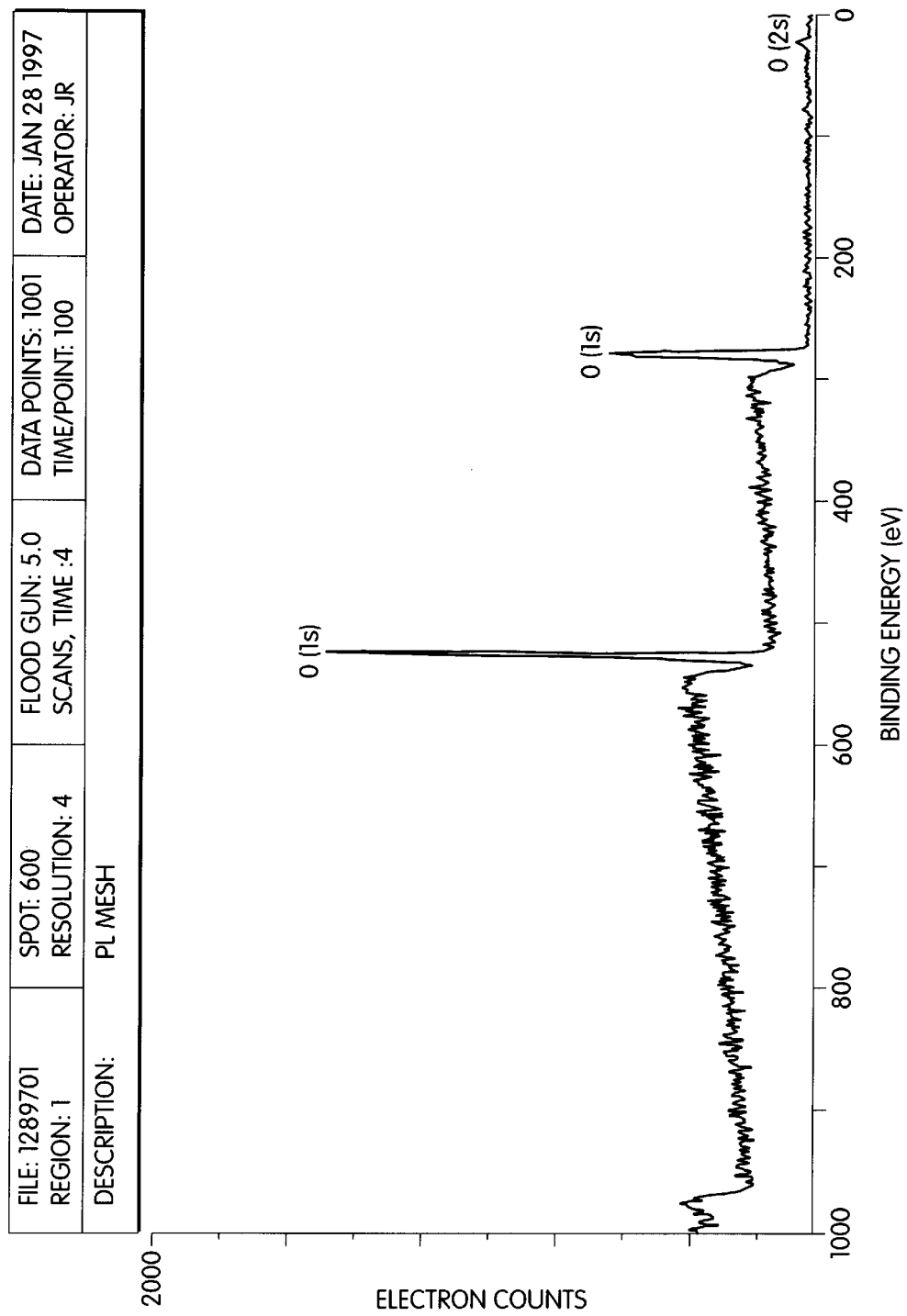
FIG. 8 is an electron spectroscopy chemical analysis spectrum of the surface of a matrix of the invention showing carbon and oxygen content.

The method for preparing the polymer matrix was repeated, using PLLA as the polymer. Electron spectroscopy for chemical analysis (ESCA) was used to analyze the top 20–25 Å of the exterior face of the matrix prepared. As shown in FIG. 8, the oxygen/carbon ratio is approximately 2:3. This value is close to the theoretical value for PLLA, which has a ratio of oxygen atoms to carbon atoms of 2:3. This result indicates that there is very little, if any, paraffin remaining on the exterior face of the matrix.

EXAMPLE 3

Growth of Bovine Bone Marrow Stromal Cells on Polymer Matrix

Phase I: Cell Isolation and Expansion

Figure 9:
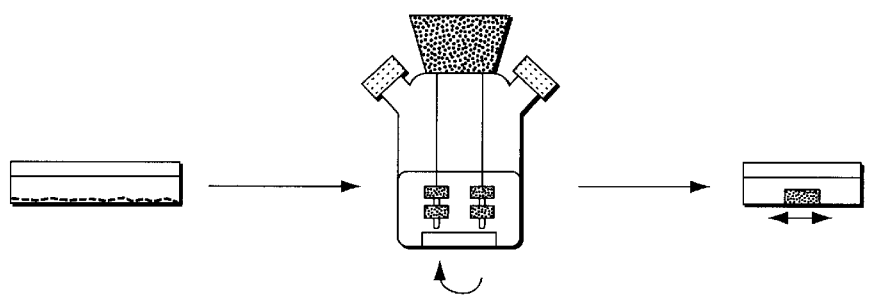
FIG. 9 is a schematic representation of the process used to grow cell and polymer constructs.

Bone marrow cultures were established from the tibia and femur of 2–3 week old bovine calves. The contents of the bone marrow cavity were aseptically harvested in Dulbecco's Modified Eagle Medium (DMEM). Single cell suspensions were made by repeatedly passing the marrow through needles of different gauges (16 to 20); the cells were then resuspended in DMEM supplemented with 10% fetal bovine serum (FBS), 0.1 mM nonessential amino acids (NEAA), 100 U/ml penicillin and 100 mg/L streptomycin (P/S). The white blood cells were counted using a hemocytometer, plated in 100 mm Petri dishes at 2×10⁶ cells per dish (approximately 25×10³ cells/cm$^2$) in 10 ml of medium supplemented with 1 ng/ml fibroblast growth factor-2 (FGF-2, also called bFGF), and cultured in a humidified 37° C./5% $CO_2$ incubator (FIG. 9, phase I).

Bone Marrow Stromal Cells (BMSC) were selected based on their ability to adhere to the Petri dish. Non-adherent hematopoietic cells were removed with the culture medium during refeeding. The medium was changed after 3 days, then twice per week thereafter. When the BMSC became near confluent (approximately 2–3 weeks after the primary culture was established), they were detached using 0.25% trypsin/1 mM ethylenediamine tetraacetic acid (EDTA), then replated in 100 mm dishes at 3×10⁵ cells per dish. After 1 more week, when the dishes again became confluent, 1st passage (P1) cells were trypsinized and seeded onto polymer scaffolds.

Phase II: Cell Seeding onto Polymer Scaffolds

Prior to cell seeding, the polymer scaffolds were pre-wetted in culture medium, threaded onto needles (1–2 scaffolds per needle, 1–2 needles per flask), positioned using 3 mm segments of silicone tubing, and fixed to a stopper in the mouth of a 25 ml spinner flask. The flasks were filled with 30 ml of medium, placed in a humidified 37° C./5% $CO_2$ incubator with the side arm caps loosened to permit gas exchange, and magnetically stirred at 75 rpm. After 2 hours, the flasks were inoculated with 3×10⁶ BMSC per scaffold (FIG. 9, phase II). FGF-2 (1 ng/ml) was added to the culture medium in this phase to increase the proliferation rate and to maintain the osteogenic potential of BMSC.

Constructs composed of scaffolds with various additives incorporated were prepared. The control construct was cultured on a scaffold composed of PGA mesh. A second construct (Sample A) was cultured on a matrix of PLA/PEG (80:20). A third construct (Sample B) was also cultured on a scaffold of PLA/PEG (80:20). A fourth construct (Sample C) was cultured on a scaffold composed of PLA/PEG (80:20), with calcium carbonate added.

Phase III: 3D Construct Cultivation

After 3 days, when cell attachment to the scaffolds was complete (as inferred from the absence of cells in the culture medium), the cell-polymer constructs were transferred to 35 mm diameter dishes coated with a thin layer of 1% agarose and placed on an orbital shaker (75 rpm) for further cultivation (FIG. 9, phase III). Each construct was cultured in 5 ml of DMEM containing 10% FBS, 0.1 mM NEAA, 50 mg/L ascorbic acid, 0.4 mM proline and P/S. In this phase, FGF-2 was not added to the culture medium. In some groups, the medium was further supplemented with 7 mM β-glycerophosphate (bGP) and $10^{-8}$ M dexamethasone (dex) to induce mineralization and osteogenic differentiation. The medium was completely replaced twice per week. The compositions of the constructs are summarized in Table 2.

TABLE 2

Composition of constructs

| Sample | Matrix polymer | Matrix additive | Culture medium additive |
|---|---|---|---|
| Control | PGA mesh | | FBS, NEAA, ascorbic acid, proline, P/S |
| A | PLA/PEG (80:20) | | FBS, NEAA, ascorbic acid, proline, P/S |
| B | PLA/PEG (80:20) | | FBS, NEAA, ascorbic acid, proline, P/S bGP, dex |

TABLE 2-continued

Composition of constructs

| Sample | Matrix polymer | Matrix additive | Culture medium additive |
|---|---|---|---|
| C | PLA/PEG (80:20) | calcium carbonate | FBS, NEAA, ascorbic acid, proline, P/S bGP, dex |

Results

Figure 10A:
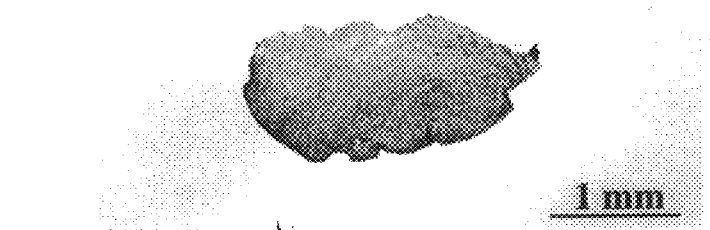
FIGS. 10A and 10C are photographs of cross sections of a conventional bovine bone marrow cell and PGA mesh construct.
Figure 10B:
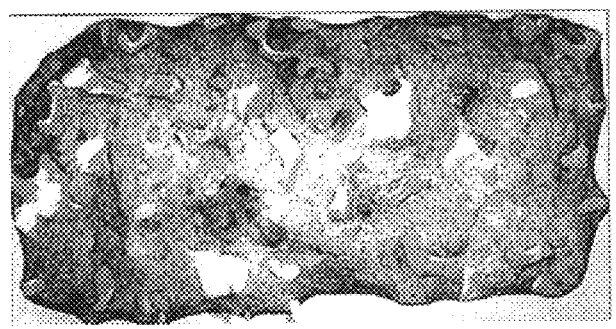
FIGS. 10B and 10D are photographs of cross sections of a bovine bone marrow cell and PLA/PEG matrix construct made with matrices of the invention.
Figure 10C:
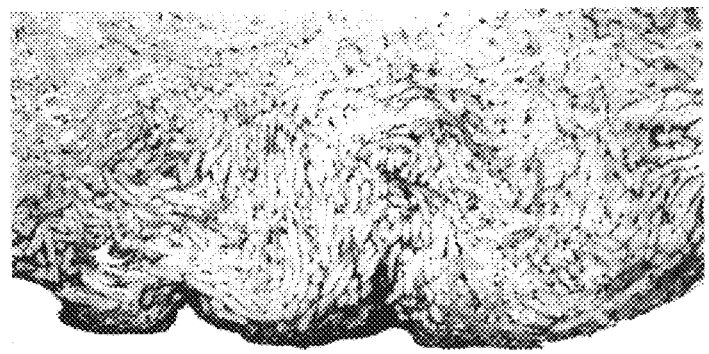
Figure 10D:
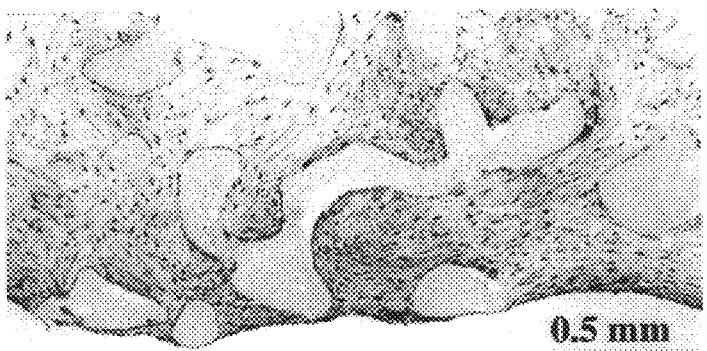

After 4 weeks in culture, the cell-polymer constructs of Samples A, B, and C maintained the initial size and shape of the scaffold, and were completely colonized by cells (FIGS. 10B, 10D). The sample grown on the PGA control mesh contracted and collapsed into a small mass that consisted primarily of undegraded polymer (FIG. 10A). The original size of the scaffold is shown by the dotted lines in these figures.

Figure 11A:
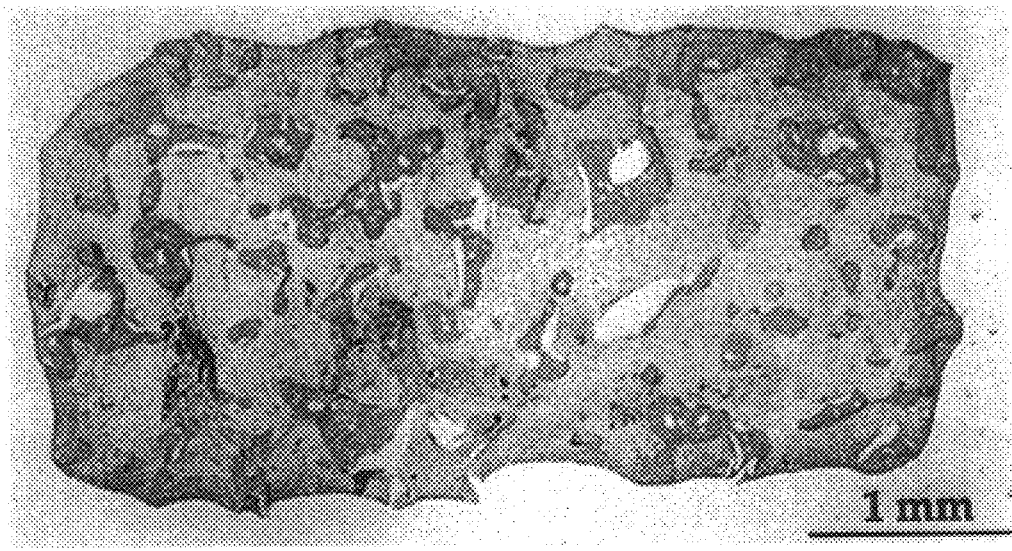
FIGS. 11A–11C are photographs of matrices of the invention with cells.
Figure 11B:
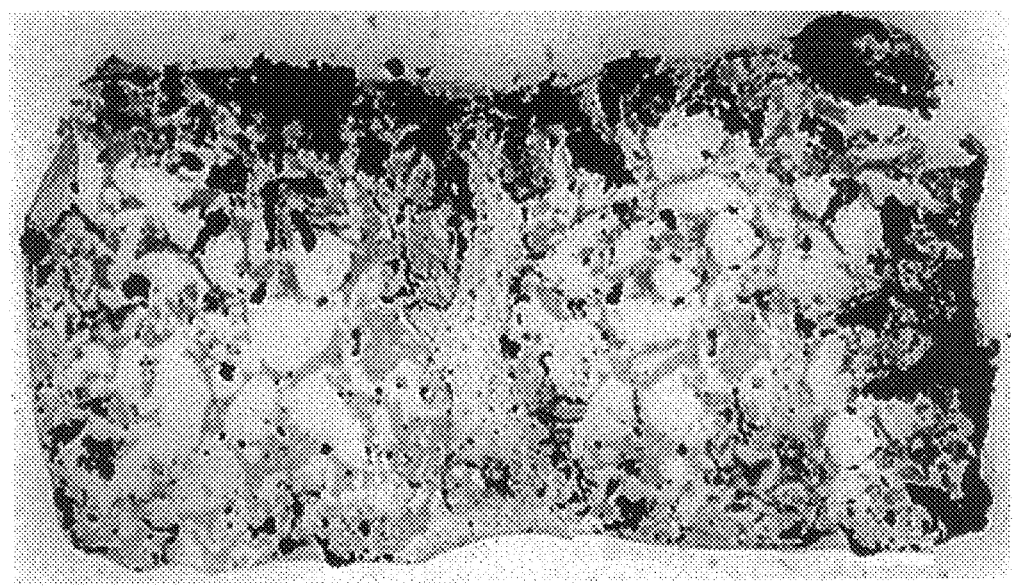
Figure 11C:
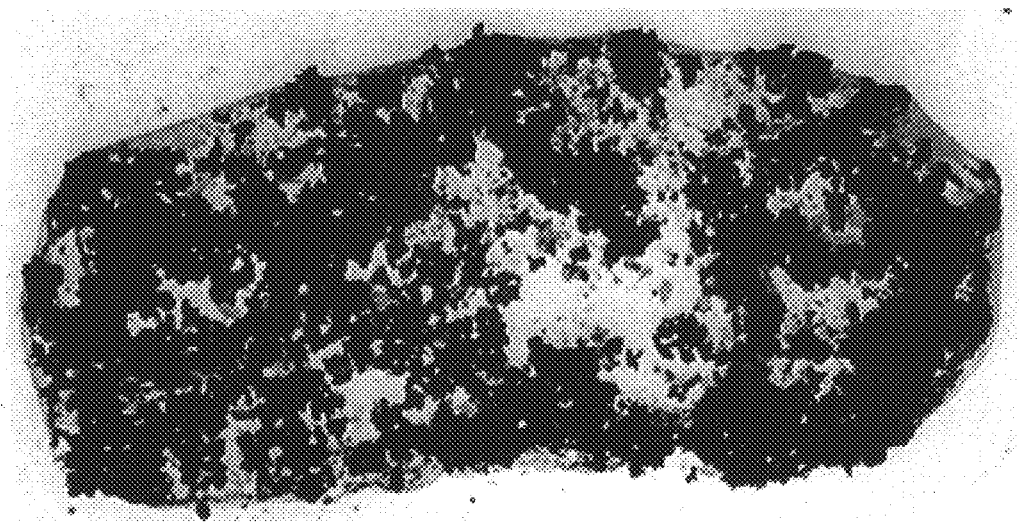

Cross-sections of the constructs were stained with alizarin red. The background intensity of the stain was negligible, as assessed using a section of a non-mineralized sample (FIG. 11A). Multicenter formation of mineralized foci was observed throughout the extracellular matrix (ECM) in the constructs that were cultured on PLA/PEG (80:20) matrices in the presence of bGP and dex (FIG. 11B). The construct that was cultured on a matrix composed of PLA/PEG (80:20) with calcium carbonate added, in the presence of β-glycerophosphate and dex, showed even more mineralization (FIG. 11C), while the control construct showed negligible mineralization (FIG. 11A).

These observations exhibit the ability of the matrices of the invention to maintain their sizes and shapes in the presence of cells; they also highlight the effects of different additives that can be incorporated in the matrices.

EXAMPLE 4

Human Bone Marrow Stromal Cells

Figure 12:
FIG. 12 is a photograph of a cross section of a human bone marrow stromal cell and PLA/PEG construct made with a matrix of the invention.

Human BMSC were isolated and expanded as described in I. Martin et al., *Endocrinology* 138:4456–4462 (1997). They were then seeded onto polymer scaffolds as described in Example 3, and cultured during Phase III using a culture medium composition formulated to induce chondrogenic differentiation of BMSC (described in F. P. Barry et al., *Trans Orthop Res Soc* 228:38, (1997)). Histological and immunohistochemical (collagen type II stain) results showed that after 3 weeks, the BMSC were able to differentiate into chondrocytes and to produce a cartilaginous ECM containing collagen type II (FIG. 12). This result indicates that the three-dimensional architecture of the polymer scaffold provides a defined, temporary structure for cell attachment. At the same time, it allows for the establishment of cell-to-cell contacts, which are thought to initiate the differentiation into chondrocytes.

EXAMPLE 5

Bovine Chondrocytes

Articular cartilage was harvested aseptically from the femoropatellar grooves of knee joints from 2–3 week old bovine calves. The tissue was chopped into 2 mm cubes for cell isolation. Chondrocytes were isolated by digestion with type II collagenase as described in L. E. Freed et al., *J Biomed Mat Res* 27:11–23 (1993). The cells were resuspended in DMEM containing 10% FBS, 0.1 mM NEAA, 0.4 mM proline, 50 mg/L ascorbic acid, and P/S.

Cell seeding was performed as described for the BMSC (FIG. 9, Phase II). Four constructs were prepared. The control sample was grown on a PGA mesh. Sample A was grown on a matrix composed of PLA; Sample B was grown on a matrix of PLA/PEG (80:20); and Sample C was grown on a matrix of PLA/PEG (60:40).

$5 \times 10^6$ cells per scaffold were seeded and cultured without the addition of FGF-2. After 3 days, the cell-polymer constructs were transferred to 35 mm diameter dishes coated with 1% agarose and placed on an orbital shaker (75 rpm) for further cultivation (FIG. 9, Phase III).

Results

Figure 13A:
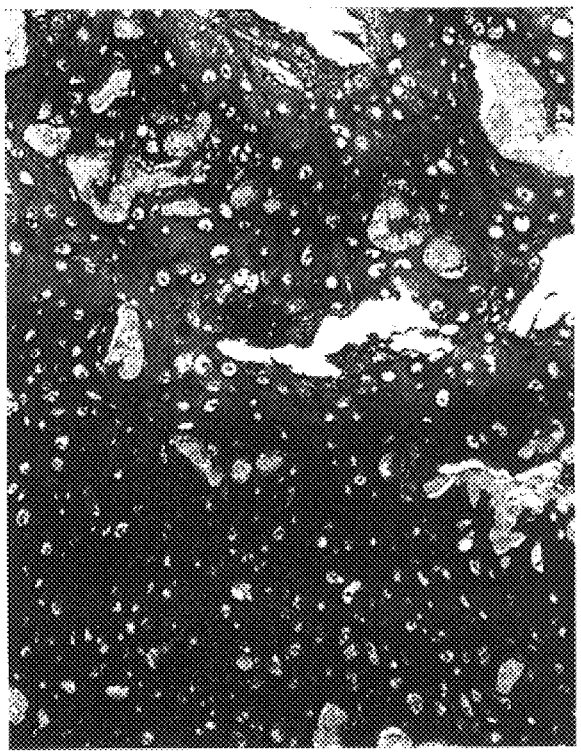
FIG. 13A is a photograph of a cross section of a bovine chondrocyte and PLA/PEG construct made with a matrix of the invention.
Figure 13B:
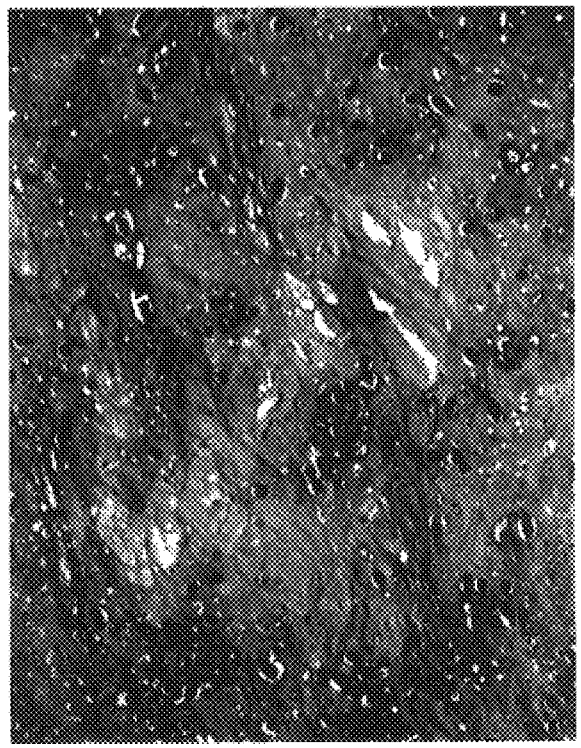
FIG. 13B is a photograph of a cross section of a conventional bovine chondrocyte and PGA mesh construct.

Chondrocytes seeded on the polymer scaffolds were able to colonize the entire scaffold and to produce cartilaginous extracellular matrix (ECM) rich in sulfated glycosaminoglycans (GAG) and in collagen type II, as assessed in tissue cross-sections stained with Safranin-O for GAG and by immunohistochemistry. The chondrocytes were also able to retain their differentiated phenotype in the inner tissue phase (FIG. 13A). The differentiated phenotypes were not observed in the samples grown on the control PGA mesh (FIG. 13B).

Figure 14A:
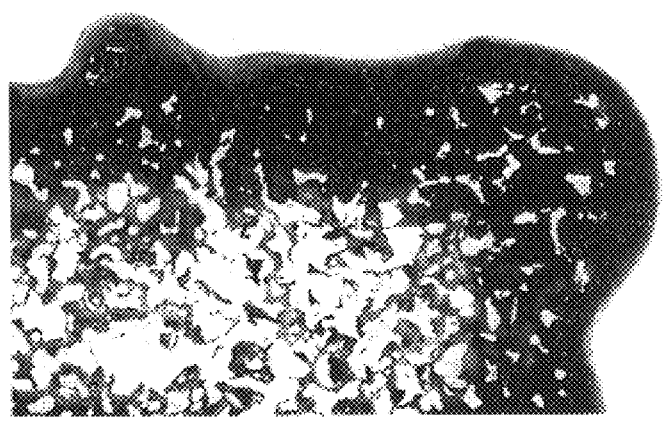
FIGS. 14A–14C are photographs of matrices of the invention with cells.
Figure 14B:
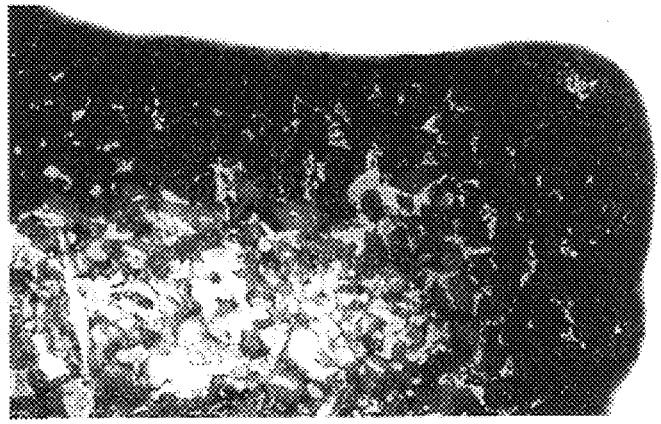
Figure 14C:
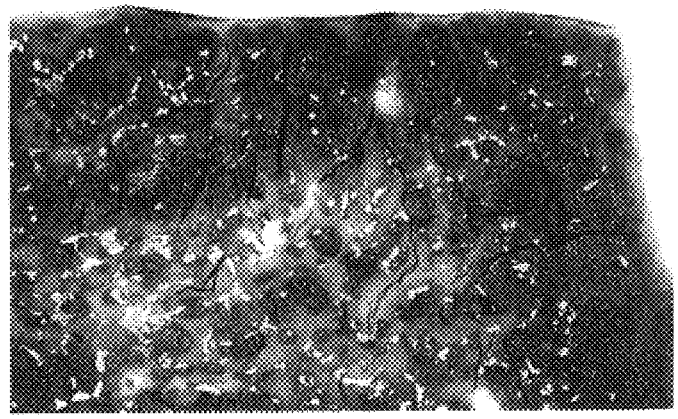

The amount of residual matrix was also measured. After 4 weeks in culture, the amount of non-resorbed polymer was significantly lower in the samples containing higher percentages of PEG (Table 3). Thus, the matrices that showed faster degradation rates corresponded to the matrices that allowed for higher extracellular matrix homogeneity produced by the cells growing in the matrix (FIGS. 14A–14C).

TABLE 3

Percentage of non-resorbed polymer

| Material | % non-resorbed polymer |
|---|---|
| PLA (Sample A, FIG. 14A) | 22.7 |
| PLA-PEG (80-20) (Sample B, FIG. 14B) | 12.0 |
| PLA-PEG (60-40) (Sample C, FIG. 14C) | 4.7 |

EXAMPLE 6

Artificial Nose

Figure 15A:
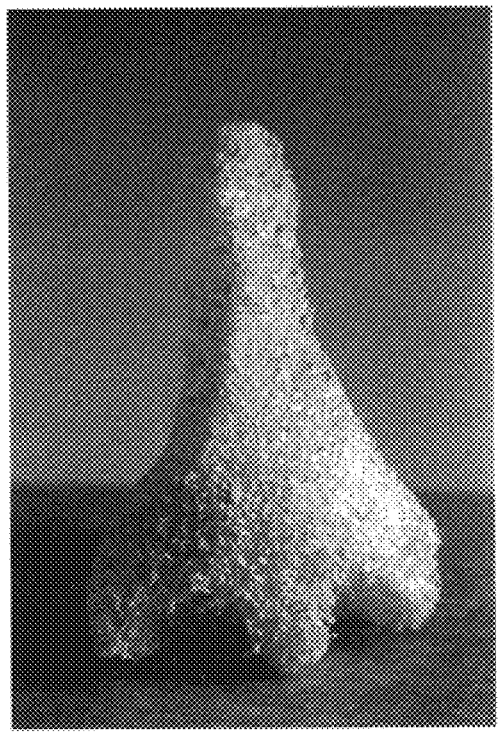
FIG. 15A is a photograph of a PLA scaffold of the invention in the shape of a human nose.
Figure 15B:
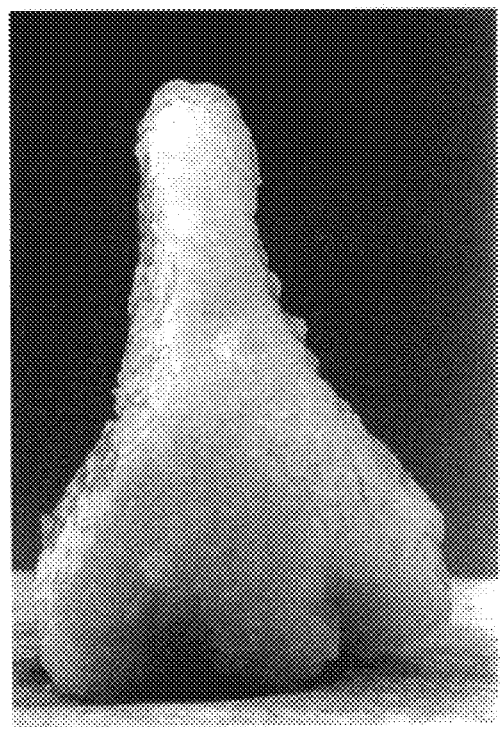
FIG. 15B is a photograph of the same scaffold two weeks after bovine chondrocytes were added.

A PLA scaffold in the shape of a human nose was carved and seeded with bovine chondrocytes. After 2 weeks, the pores were completely filled with cartilaginous matrix; at the same time, the scaffold was able to retain its complex geometry (FIGS. 15A and 15B).

EXAMPLE 7

Variation of Mechanical Properties

Six different polymer matrices were prepared, using different polymer compositions: PLGA, PLLA, and PMMA, PLGA/PEG, PLA/PEG, and PLA/PEG/CaCO$_3$. The mechanical properties were measured using a Dynamic Mechanical Analyzer, using disc-shaped samples having a diameter of 4–7 mm and a thickness of 2–4 mm. Stress is the amount of force applied to the sample; strain is the amount by which the sample compresses.

Figure 16:
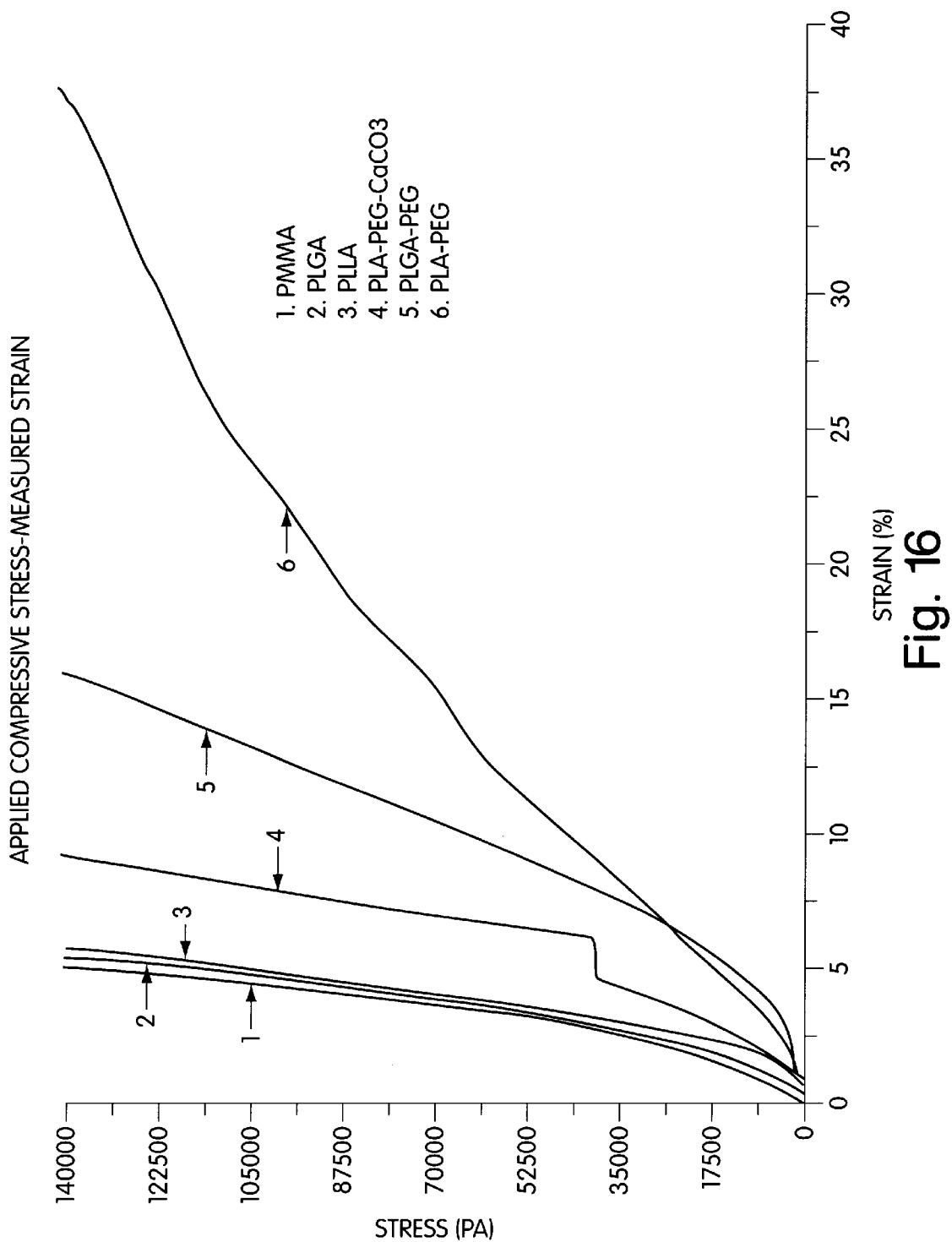
FIG. 16 is a graph showing mechanical properties of polymer and polymer blend matrices.

As shown in FIG. 16, samples containing PLGA, PLLA, and PMMA compressed by about 5% when subjected to a stress of 140,000 Pa. A sample containing PLA/PEG/CaCO$_3$ compressed by about 9%. Samples that were made with blends of PLGA/PEG (80:20) and PLA/PEG (80:20) compressed by about 16% and 38%, respectively. The samples of both blends returned to within 5% of their original size within one minute. The sample of PLGA/PEG (80:20) returned to essentially 100% of its original size substantially instantaneously. These results demonstrate the effects that different polymer compositions have on the mechanical properties of the matrices.

Table 4 summarizes additional mechanical properties of the matrices.

TABLE 4

Mechanical properties of polymer and polymer blend matrices

| Material | Modulus (MPa) at 4% strain | Strain at 140 KPa | Modulus (Mpa) 140 KPa stress |
|---|---|---|---|
| PMMA | 5.356 | 4.9 | 5.036 |
| PLGA | 4.136 | 5.28 | 5.115 |
| PLGA-PEG (80-20) | 0.499 | 15.8 | 1.333 |
| PLA | 4.048 | 5.58 | 4.57 |
| PLA-PEG (80-20) | 0.537 | 37.41 | 0.383 |
| PLA-PEG (80-20)-CaCO$_3$ | 1.239 | 9.01 | 2.968 |

EXAMPLE 8

Controlled Release of Alkaline Phosphatase

In the control sample, PEG was dissolved in PBS buffer. Alkaline phosphatase (ALP) was added and the mixture was lyophilized to form a powder. After lyophilization, the ALP activity was below detection levels.

PEG (200 mg) and alkaline phosphatase (ALP) (1000 units) were dissolved in about 1 mL of PBS buffer containing 1.0% bovine serum albumin (BSA). The mixture was frozen and lyophilized to form a powder. The ALP activity of the powder was 0.557 units/mg, which represents a loss of about 9-fold with respect to the initial enzymatic activity.

Figure 17:
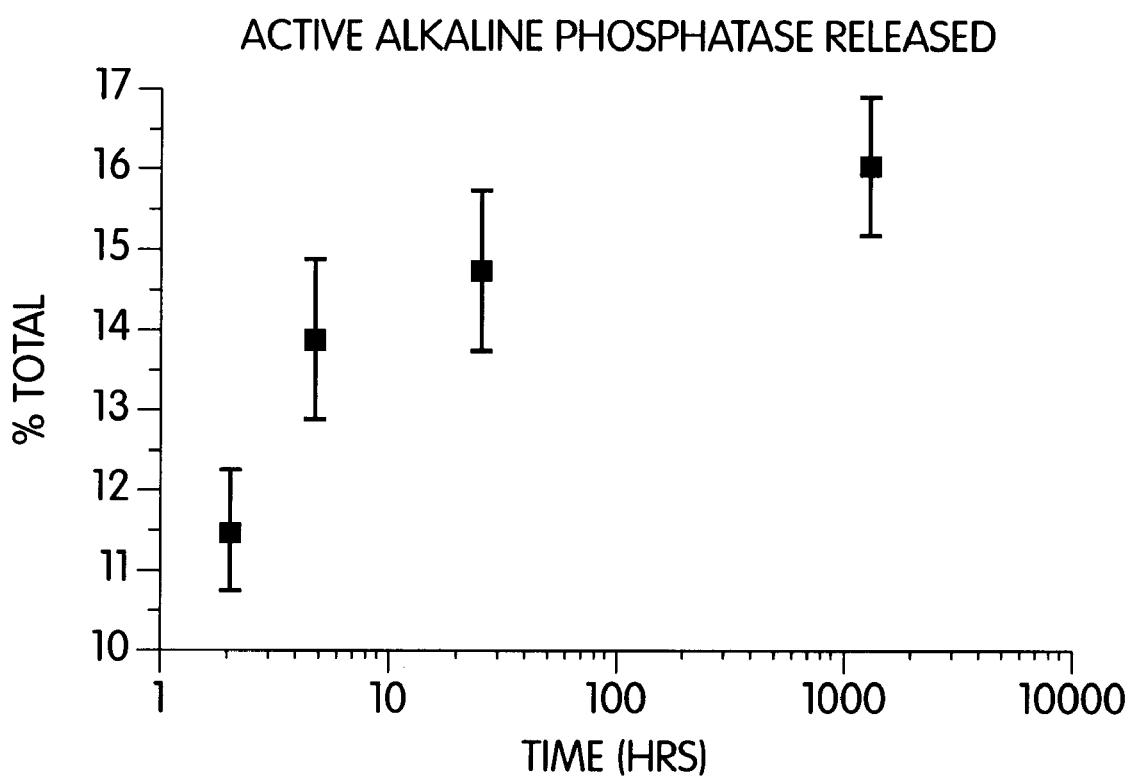
FIG. 17 is a graph showing ALP release from a PLA/PEG matrix.

The PLA/PEG (80:20) matrices were loaded with ALP using the PEG/ALP mixture described above and incubated at 4° C. in PBS buffer containing 1.0% bovine serum albumin (BSA) for up to 7 weeks. Samples of the solution were taken at timed intervals and assayed for ALP activity (Sigma kit No. 245). ALP activity was expressed as active units per mg of initial construct weight. The results are shown in FIG. 17. As shown there, ALP can be released from the matrix for extended periods of time; for example, ALP can be released for up to 1000 hours. The release time can be controlled by loading different amounts of ALP. The more ALP that is loaded on a matrix, the longer the release time.

EXAMPLE 9

Polymer Blends

Matrices made of polymer blends, with and without inorganic additives, were prepared using the general techniques described above. The following table summarizes the blends that were prepared, as well as their physical properties.

TABLE 5

Polymer and polymer blend matrices

| Polymer Composition (Ratios are wt %) | Polymer MW | Total Polymer Weight | Additives WT % of Total Polymer | Bulk Properties Density (d), Resistivity (r) |
|---|---|---|---|---|
| PLLA | 90,000–100,000 | 200 mg | None | d = 130–140 mg/cc |
| PLGA (85:15) | 128,000 | 200 mg | None | d = 130–150 mg/cc |
| PEG | 100,000 | 300 mg | None | d = 220–260 mg/cc |
| PMMA | 120,000 | 200 mg | None | d ≈ 160 mg/cc |
| PLLA + PEG (80:20) | 100,000 & 20,000 | 200 mg | None | d = 105–150 mg/cc |
| PLLA + PEG (80:20) | 100,000 & 10,000 | 200 mg | None | d = 105–150 mg/cc |
| PLLA + PEG (80:20) | 100,000 & 6,000 | 200 mg | None | d = 105–150 mg/cc |
| PLLA + PEG (80:20) | 100,000 & 20,000 | 200 mg | None | d = 105–150 mg/cc |

TABLE 5-continued

Polymer and polymer blend matrices

| Polymer Composition (Ratios are wt %) | Polymer MW | Total Polymer Weight | Additives WT % of Total Polymer | Bulk Properties Density (d), Resistivity (r) |
|---|---|---|---|---|
| PLLA + PEG (80:20) | 100,000 & 20,000 | 200 mg | ~5 mg, Rhodamine-B | d = 105–150 mg/cc |
| PLLA + PEG (80:20) | 100,000 & 20,000 | 200 mg | Alkaline Phosphatase (ALP) 200 units | d = 105–150 mg/cc |
| PLLA + PEG (80:20) | 100,000 & 10,000 | 200 mg | 25% FITC-Dextran (MW = 71,200) | d = 105–150 mg/cc |
| PLLA + PBG (80:20) | 100,000 & 20,000 | 200 mg | 50% Calcium Carbonate (particle size <53 μm) | d = 170–190 mg/cc |
| PLLA + PEG (80:20) | 100,000 & 20,000 | 200 mg | 50% beta-Glycerophosphate | d = 170–200 mg/cc |
| PLLA | 100,000 | 200 mg | 50% Unfired Hydroxyapatite (particle size 45–70 μm) | d = 200 mg/cc |
| PLLA | 100,000 | 200 mg | 50% Hydroxy Apatite (FinCeramica, particle size 212–500 μm) | d = 200 mg/cc |
| PLLA | 100,000 | 200 mg | 100% Hydroxy Apatite (FinCeramica, particle size 212–500 μm) | d ≈ 300 mg/cc |
| PLGA + PEG (80:20) | 128,000 & 100,000 | 200 mg | None | d = 130–150 mg/cc |
| PLGA + PEG (80:20) | 128,000 & 20,000 | 200 mg | None | d = 130–150 mg/cc |
| PLGA + PEG (80:20) | 128,000 & 20,000 | 200 mg | ~5 mg, Rhodamine-B | d = 130–150 mg/cc |
| PMMA | 120,000 | 300 mg | 30 mg, Colloidal Graphite | d = 250–300 mg/cc, No Conductivity |
| PMMA | 120,000 | 290 mg | 100 mg, Colloidal Graphite | d = 274 mg/cc, r = 4.96 KΩ-cm |
| PMMA | 120,000 | 250 mg | 200 mg, Colloidal Graphite | d = 358 mg/cc, r = 0.840 KΩ-cm |
| PMMA | 120,000 | 200 mg | 100 mg, Micronized Polyethylene | d ≈ 300 mg/cc |

All publications and patents mentioned in this specification are herein incorporated by reference to the same extent as if each individual publication or patent was specifically and individually indicated to be incorporated by reference.

Other Embodiments

From the foregoing description, it will be apparent that variations and modifications may be made to the invention described herein to adopt it to various usages and conditions. Such embodiments are also within the scope of the following claims.

What is claimed is:

1. A matrix comprising a macrostructure having a substantially continuous semi-solid network and voids, said matrix further comprising a microstructure having voids, wherein said microstructure is located within said semi-solid network.

2. The matrix of claim 1, wherein said semi-solid network comprises a polymer.

3. The matrix of claim 1, wherein said matrix comprises a copolymer having a carboxylic acid group or a copolymer having an amine group.

4. The matrix of claim 1, wherein said matrix comprises a conductive polymer selected from the group consisting of polypyrrole, polyaniline, polyacetylene, and polythiophene.

5. The matrix of claim 1, wherein said semi-solid network consists essentially of a polymer or mixture of polymers.

6. The matrix of claim 1, wherein the surface area of said matrix is at least 1 m$^2$/g.

7. The matrix of claim 1, wherein said voids of said macrostructure are substantially continuous.

8. The matrix of claim 1, wherein at least 10% of said voids of said macrostructure and said voids of said microstructure are connected.

9. The matrix of claim 1, wherein said voids of said macrostructure and said voids of said microstructure are not connected.

10. The matrix of claim 1, said voids of said macrostructure defining openings, wherein the average diameter of said openings and the average diameter of the cross-sections of said semi-solid network have a ratio of from 2:1 to 10:1.

11. The matrix of claim 10, wherein said ratio is from 2:1 to 5:1.

12. The matrix of claim 1, wherein the semi-solid network of a cubic portion of said matrix having dimensions of 0.5 cm on all sides and having voids defining openings having an average diameter of 50–500 μm has a connectivity number of at least 10.

13. The matrix of claim 12, wherein said connectivity number is at least 20.

14. The matrix of claim 1, a cross section of said semi-solid network having a maximum and a minimum diameter, wherein the ratio of said maximum diameter and said minimum diameter is from 1:1 to 10:1.

15. The matrix of claim 1, wherein at least 10% of the voids of said microstructure have a fractal dimension of at least 3.

16. The matrix of claim 15, wherein less than 10% of the voids of said macrostructure have a fractal dimension higher than 1.

17. The matrix of claim 1, wherein said matrix is three dimensional.

18. The matrix of claim 1, wherein the exterior face of said matrix is porous.

19. The matrix of claim 1, wherein said matrix has a porosity of at least about 20%.

20. The matrix of claim 1, wherein said matrix is biodegradable.

21. The matrix of claim 1, wherein said matrix is bioerodible.

22. The matrix of claim 1, wherein said matrix is bioresorbable.

23. The matrix of claim 1, wherein said matrix is impermeable to cells.

24. The matrix of claim 1, wherein said matrix is permeable to bodily fluids.

25. The matrix of claim 1, wherein said matrix is permeable to cells.

26. The matrix of claim 1, wherein said matrix further comprises a living cell.

27. The matrix of claim 1, wherein said matrix changes in size less than 50% when cells are added to said matrix.

28. The matrix of claim 1, wherein said matrix has a compressive modulus of at least 0.4 MPa at 4% strain.

29. The matrix of claim 1, wherein said matrix has a density of less than about 0.150 g/cc.

* * * * *